(12) United States Patent
Matsuzawa et al.

(10) Patent No.: US 10,624,335 B2
(45) Date of Patent: Apr. 21, 2020

(54) TOOL FOR CRYOPRESERVATION OF CELL OR TISSUE AND CRYOPRESERVATION METHOD

(71) Applicant: MITSUBISHI PAPER MILLS LIMITED, Tokyo (JP)

(72) Inventors: Atsushi Matsuzawa, Tokyo (JP); Katsumitsu Susaki, Tokyo (JP); Yukio Tokunaga, Tokyo (JP)

(73) Assignee: MITSUBISHI PAPER MILLS LIMITED, Tokyo (JP)

( * ) Notice: Subject to any disclaimer, the term of this patent is extended or adjusted under 35 U.S.C. 154(b) by 159 days.

(21) Appl. No.: 15/520,637

(22) PCT Filed: Oct. 16, 2015

(86) PCT No.: PCT/JP2015/079324
§ 371 (c)(1),
(2) Date: Apr. 20, 2017

(87) PCT Pub. No.: WO2016/063806
PCT Pub. Date: Apr. 28, 2016

(65) Prior Publication Data
US 2017/0311587 A1    Nov. 2, 2017

(30) Foreign Application Priority Data

Oct. 23, 2014 (JP) .................. 2014-216350
Sep. 14, 2015 (JP) .................. 2015-180310
(Continued)

(51) Int. Cl.
*A01N 1/02* (2006.01)
*A61J 3/00* (2006.01)
(Continued)

(52) U.S. Cl.
CPC .......... *A01N 1/0221* (2013.01); *A01N 1/021* (2013.01); *A01N 1/0231* (2013.01);
(Continued)

(58) Field of Classification Search
None
See application file for complete search history.

(56) References Cited

U.S. PATENT DOCUMENTS

| 4,245,744 A | 1/1981 | Daniels et al. |
| 5,981,044 A | 11/1999 | Phan et al. |

(Continued)

FOREIGN PATENT DOCUMENTS

| CN | 101111603 A | 1/2008 |
| CN | 101400784 A | 4/2009 |

(Continued)

OTHER PUBLICATIONS

Steponkus, P.L. et al., "Cryopreservation of *Drosophila melanogaster* embryos" Letters to Nature, vol. 345, p. 170-172, dated May 10, 1990 (3 pages).

(Continued)

*Primary Examiner* — Allison M Fox
*Assistant Examiner* — Qing Xu
(74) *Attorney, Agent, or Firm* — Osha Liang LLP

(57) ABSTRACT

The present invention relates to a device for cryopreservation of a cell or tissue, including a deposition part on which a cell or tissue is to be deposited, the deposition part having a layer containing a water-soluble polymeric compound on an outermost surface of the deposition part; and a method of cryopreservation using the device.

6 Claims, 5 Drawing Sheets

(30) Foreign Application Priority Data

Sep. 16, 2015 (JP) ................................ 2015-182373
Sep. 25, 2015 (JP) ................................ 2015-187967

(51) Int. Cl.
*C12M 3/00* (2006.01)
*C12N 1/04* (2006.01)
*C12M 1/00* (2006.01)

(52) U.S. Cl.
CPC ......... *A01N 1/0236* (2013.01); *A01N 1/0268* (2013.01); *A61J 3/00* (2013.01); *C12M 1/00* (2013.01); *C12M 3/00* (2013.01); *C12N 1/04* (2013.01)

(56) References Cited

U.S. PATENT DOCUMENTS

| | | | |
|---|---|---|---|
| 6,145,504 | A | 11/2000 | Miyake |
| 6,638,755 | B1 | 10/2003 | Mizuochi et al. |
| 9,516,876 | B2 | 12/2016 | Inoue |
| 2001/0039406 | A1 | 11/2001 | Hamajima et al. |
| 2004/0065093 | A1 | 4/2004 | Fuhr et al. |
| 2004/0235182 | A1 | 11/2004 | Jones |
| 2009/0221047 | A1 | 9/2009 | Schindler et al. |
| 2009/0311297 | A1 | 12/2009 | Hontsu et al. |
| 2010/0151174 | A1 | 6/2010 | Graff et al. |
| 2012/0251752 | A1 | 10/2012 | Hayashi et al. |
| 2016/0057991 | A1 | 3/2016 | Matsuzawa et al. |
| 2016/0236412 | A1* | 8/2016 | Kusahara ............ B28B 7/465 |
| 2017/0135335 | A1 | 5/2017 | Matsuzawa et al. |

FOREIGN PATENT DOCUMENTS

| | | |
|---|---|---|
| CN | 101522856 A | 9/2009 |
| CN | 102753677 A | 10/2012 |
| CN | 103179852 A | 6/2013 |
| CN | 203340879 U | 12/2013 |
| CN | 203369308 U | 1/2014 |
| EP | 3064567 A1 | 9/2016 |
| JP | H02-117381 A | 5/1990 |
| JP | H03-289955 A | 12/1991 |
| JP | H05-176946 A | 7/1993 |
| JP | H07-289235 A | 11/1995 |
| JP | H10-121021 A | 5/1998 |
| JP | H10-248860 A | 9/1998 |
| JP | 2000000251 A | 1/2000 |
| JP | 3044323 B1 | 5/2000 |
| JP | 2000212532 A | 8/2000 |
| JP | 2000325072 A | 11/2000 |
| JP | 2002315573 A | 10/2002 |
| JP | 2003311892 A * | 11/2003 |
| JP | 2004018504 A | 1/2004 |
| JP | 2005040073 A | 2/2005 |
| JP | 2006521823 A | 9/2006 |
| JP | 2006271395 A | 10/2006 |
| JP | 2008005846 A | 1/2008 |
| JP | 2008222640 A | 9/2008 |
| JP | 2009526527 A | 7/2009 |
| JP | 2009240816 A | 10/2009 |
| JP | 2012219017 A | 11/2012 |
| JP | 2013111017 A | 6/2013 |
| JP | 5278978 B2 | 9/2013 |
| JP | 2014100111 A | 6/2014 |
| JP | 2014183757 A | 10/2014 |
| JP | 2015188405 A | 11/2015 |
| WO | 2006058286 A2 | 6/2006 |
| WO | 2008018966 A2 | 2/2008 |
| WO | 2011070973 A1 | 6/2011 |
| WO | 2011146998 A1 | 12/2011 |
| WO | 2013051521 A1 | 4/2013 |
| WO | 2013/117925 A1 | 8/2013 |
| WO | 2014185457 A1 | 11/2014 |
| WO | 2015115313 A1 | 8/2015 |

OTHER PUBLICATIONS

Anan, Taku et al., "Vitrification of bovine blastocysts for direct transfer by absorption removal of surrounding vitrification solution" Japanese Society of Animal Science Annual Meeting Abstracts, vol. 112, p. 88, dated Mar. 28, 2010 (5 pages).
Extended European Search Report issued in European Application No. 15852360.5, dated May 30, 2018 (7 pages).
Akira Sakai, "Cryopreservation of Cultured Plant Cells and Meristems by Vitrification", Cryobiology and Cryotechnology, vol. 42, No. 1, pp. 61-68 (1996) (11 pages).
International Preliminary Report on Patentability issued in International Application No. PCT/JP2014/062862; dated Nov. 26, 2015 (7 pages).
International Search Report issued in PCT/JP2015/065754, dated Aug. 4, 2015 (2 pages.).
Written Opinion of the International Searching Authority issued in PCT/JP2015/065754, dated Aug. 4, 2015 (4 pages).
Momozawa, K. et al., "Vitrification of bovine blastocysts on a membrane filter absorbing extracellular vitrification solution" J. Mamm. Ova Res., Apr. 1, 2006, vol. 23, No. 1, pp. 63-66 (5 pages).
Japanese Society of Animal Science Annual Meeting Abstracts, vol. 112th, p. 88, Mar. 28, 2010 (5 pages).
Lee, Kung-Hsiung et al., "An efficient and mass reproducible method for vitrifying mouse embryos on a paper in cryotubes," Cryobiology, Academic Press Inc., US, vol. 66, No. 3, p. 311-317, dated Mar. 28, 2013 (7 pages).
Kim, Y.M. et al., "Successful vitrification of bovine blastocysts on paper container," Theriogenology, vol. 78, No. 5, p. 1085-1093, dated Sep. 1, 2012 (9 pages).
Office Action issued in Korean Application No. 10-2017-7000907, dated Jun. 21, 2018 (6 pages).

* cited by examiner

TOOL FOR CRYOPRESERVATION OF CELL OR TISSUE AND CRYOPRESERVATION METHOD

TECHNICAL FIELD

The present invention relates to a device for cryopreservation used for cryopreservation of, for example, cells or tissues, and a method of cryopreservation using the device.

BACKGROUND ART

Excellent preservation techniques for cells or tissues are desired in various industrial fields. For example, in the bovine embryo transfer technology, embryos are cryopreserved in advance and thawed and transferred in time with the estrus cycle of a recipient cow. In the human fertility treatment, eggs or ovaries are harvested from a woman's body and cryopreserved until an appropriate timing for transplantation, and the cryopreserved eggs or ovaries are thawed before the use in transplantation.

In general, cells or tissues harvested from living bodies gradually become inactive even in a culture medium, and hence long-term culture of cells or tissues in vitro is undesirable. For this reason, techniques for long-term preservation of cells or tissues without the loss of biological activity are essential. Excellent preservation techniques enable more accurate analysis of cells or tissues harvested. Such excellent preservation techniques also enable transplantation of cells or tissues with their biological activity kept at a higher level, thus likely resulting in an improvement in the engraftment rate. The techniques also enable in-advance production and preservation of artificial tissues for transplantation, such as skins cultured in vitro and what they call cell sheets formed in vitro, and storage thereof until needed. Therefore, such excellent preservation techniques are expected to bring great advantages not only in the medical science fields but also in the industrial fields.

One of known methods for preserving cells or tissues is slow freezing, for example. In this method, cells or tissues are immersed in a preservation solution prepared by adding a cryoprotectant to a physiological solution such as phosphate buffered saline. Examples of the cryoprotectant include compounds such as glycerol and ethylene glycol. The cells or tissues immersed in the preservation solution are cooled down to −30° C. to −35° C. at a relatively slow cooling rate (for example, 0.3° C. to 0.5° C./min), and thereby the solution inside and outside the cells or tissues are sufficiently cooled and become viscous. Further cooling down the cells or tissues in such a state in the preservation solution to the temperature of liquid nitrogen (−196° C.) allows a slight amount of the solution both inside and outside (surrounding) the cells or tissues to become a solid while the amorphous state thereof is maintained, that is, to vitrify. The vitrification (i.e., solidification) of the solution inside and outside the cells or tissues substantially immobilizes the molecules. Thus, the vitrified cells or tissues can be semipermanently preserved in liquid nitrogen.

However, since the slow freezing requires relatively slow-rate cooling, the procedure of cryopreservation takes a long time. Further, this technique disadvantageously needs the use of a temperature-controlling device or jig. In addition, the slow freezing cannot avoid formation of ice crystals in the preservation solution outside the cells or tissues, which may cause physical damage to the cells or tissues.

One proposed solution to the problems of the slow freezing is vitrification cryopreservation. The vitrification cryopreservation is a technique using a principle that addition of a large amount of a cryoprotectant, such as glycerol, ethylene glycol, or dimethyl sulfoxide (DMSO), to water decreases the freezing point of water, thereby restraining formation of ice crystals at sub-zero temperatures. When quickly cooled in liquid nitrogen, such an aqueous solution can solidify without formation of ice crystals. This solidification is called vitrification freezing. The aqueous solution containing a large amount of a cryoprotectant is called a vitrification solution.

The specific procedure of the vitrification cryopreservation is to immerse cells or tissues in a vitrification solution and to cool them at the temperature of liquid nitrogen (−196° C.). Since the vitrification is such a simple and quick process, it advantageously does not require a long-term procedure of cryopreservation or the use of any temperature-controlling device or jig.

The vitrification cryopreservation does not cause formation of ice crystals either inside or outside the cells, and thus can avoid physical damage (freezing damage) to the cells at the time of freezing and thawing. However, a high-concentration cryoprotectant contained in the vitrification solution is chemically toxic. Thus, the volume of the vitrification solution around cells or tissues used in cryopreservation of the cells or tissues is preferably as small as possible. Further, the duration of exposure of the cells to the vitrification solution, that is, the time until freezing, is preferably short. In addition, the vitrification solution needs to be diluted immediately after thawing.

Various examples of the vitrification-based cryopreservation of cells or tissues have been reported using various methods and various cells or tissues. For example, Patent Literature 1 discloses that application of the vitrification cryopreservation to reproductive or somatic cells of animal or human origin is very useful in terms of the cell viability after cryopreservation and thawing.

The vitrification cryopreservation is a technique which has been developed mainly using human reproductive cells. More recently, its application to iPS or ES cells has also been widely examined. Non-Patent Literature 1 discloses the effectiveness of the vitrification cryopreservation in preservation of *Drosophila* embryos. Patent Literature 2 discloses the effectiveness of the vitrification cryopreservation in preservation of plant culture cells and tissues. As mentioned here, the vitrification is known to be useful for preservation of a wide range and different kinds of cells and tissues.

Patent Literatures 3 and 4 propose a cryopreservation method, what is called the Cryotop method, used in the field of human fertility treatment. This method uses a tool for cryopreservation of eggs including a flexible, clear and colorless film strip as an egg-holding strip, and includes depositing eggs or embryos together with a very small amount of a vitrification solution on the film under a microscope.

Patent Literature 5 proposes a cryopreservation method with excellent viability including depositing eggs or embryos together with a vitrification solution on a removing material for vitrification preservation solution and removing an excess vitrification solution surrounding the eggs or embryos by downward suction. Examples of the removing material for vitrification preservation solution disclosed include wire mesh and perforated films made of natural substance, such as paper, or synthetic resin. Devices for cryopreservation which allow the removal of an excess vitrification solution and improve the working efficiency in the deposition of cells have also been proposed. Patent Literature 6, for example, discloses a device for vitrification cryopreservation including a vitrification solution absorber with a specific haze value.

Patent Literature 7 discloses a cell-preserving container for preserving cells together with a medium. It teaches that a container whose inner surface is formed of a material that is less likely to trap cells, specifically, a container whose inner surface is bonded or coated with a hydrophilic or hydrophobic material, can prevent cells from adhering to the container wall during preservation. Examples of hydrophilic materials disclosed include acrylamide polymers and polyvinyl alcohol. Examples of hydrophobic materials disclosed include fluororesin and silicone resin.

CITATION LIST

Patent Literature

Patent Literature 1: JP 3044323 B
Patent Literature 2: JP 2008-5846 A
Patent Literature 3: JP 2002-315573 A
Patent Literature 4: JP 2006-271395 A
Patent Literature 5: WO 2011/070973
Patent Literature 6: JP 2014-183757 A
Patent Literature 7: JP 2004-18504 A Non-Patent Literature Non-Patent Literature 1: Steponkus et al., Nature 345: 170-172 (1990)

SUMMARY OF INVENTION

Technical Problem

Patent Literatures 3 and 4 each propose a method for cryopreservation of eggs or embryos together with a small amount of a vitrification solution by limiting the width of a film on which eggs or embryos are to be deposited. In this method, a worker manually deposits eggs or embryos together with a very small amount of a vitrification solution on a film, but this operation is very difficult. In order to cryopreserve eggs or embryos together with a smaller amount of a vitrification solution, the Cryotop method based on this method sometimes includes a complicated procedure, i.e., depositing eggs or embryos together with a vitrification solution on a film and then suction-removing an excess vitrification solution from the top of the film. Furthermore, during thawing the frozen eggs or embryos, the eggs or embryos often adhere to the film. Recovering them disadvantageously requires high-level skills.

The method proposed in Patent Literature 5 is for cryopreservation of eggs or embryos with excellent viability by removing an excess vitrification solution surrounding these reproductive cells. However, the removal of an excess vitrification solution in the method disclosed in this literature requires downward suction, making the procedure complicated. Thus, this method is unsuitable for quick completion of the vitrification cryopreservation procedure. Another problem is that an excess vitrification solution may remain if the downward suction is insufficient. In addition, in thawing the frozen eggs or embryos, the eggs or embryos may adhere to the film as in Patent Literatures 3 and 4, and recovering them disadvantageously requires high-level skills. In Patent Literature 6, a worker does not need to remove an excess vitrification solution surrounding the eggs or embryos, so that good working efficiency can be achieved. However, the absorption of the vitrification solution by the vitrification solution absorber causes particularly strong adhesion of the eggs or embryos to the vitrification solution absorber. Recovering these eggs or embryos disadvantageously requires particularly high-level skills.

One main object of the present invention is to provide a device for cryopreservation of a cell or tissue which enables easy and reliable cryopreservation of a cell or tissue. Specifically, a first object of the present invention is to provide a device for cryopreservation which enables easy release and recovery of a cell or tissue in thawing the cell or tissue after it is immersed in a preservation solution such as a vitrification solution and deposited on the device together with the preservation solution and cryopreserved. A second object of the present invention is to provide a device for cryopreservation which not only enables easy recovery of a cell or tissue but also has excellent preservation solution (e.g., vitrification solution) absorbency. Another object of the present invention is to provide a cryopreservation method which enables easy release and recovery of a cell or tissue after cryopreservation.

Solution to Problem

After intensive studies to solve the above problems, the present inventors found out that a device for cryopreservation of a cell or tissue (herein, "device for cryopreservation of a cell or tissue" is also referred to simply as "device for cryopreservation") having the following configuration can solve the above problems.

(1) A device for cryopreservation of a cell or tissue, including a deposition part on which a cell or tissue is to be deposited, the deposition part having a layer containing a water-soluble polymeric compound on an outermost surface of the deposition part.

(2) The device for cryopreservation of a cell or tissue according to the above embodiment (1), wherein the water-soluble polymeric compound is at least one selected from the group consisting of a polyvinyl alcohol having an ethanediol group and a polyvinyl alcohol having an ethylene oxide group.

(3) The device for cryopreservation of a cell or tissue according to the above embodiment (1), wherein the water-soluble polymeric compound is a polyvinyl alcohol with a degree of saponification of 94 mol % or less.

(4) The device for cryopreservation of a cell or tissue according to any one of the above embodiments (1) to (3), wherein the layer containing the water-soluble polymeric compound further contains inorganic fine particles.

(5) The device for cryopreservation of a cell or tissue according to any one of the above embodiments (1) to (4), wherein the deposition part has a preservation solution absorber and has the layer containing the water-soluble polymeric compound on the preservation solution absorber.

(6) A method of cryopreservation of a cell or tissue, including: depositing a cell or tissue immersed in a preservation solution on the deposition part of the device for cryopreservation of a cell or tissue according to any one of the above embodiments (1) to (5) together with the preservation solution; and immersing the device for cryopreservation with the cell or tissue held on the deposition part into liquid nitrogen to freeze the cell or tissue.

(7) The method of cryopreservation of a cell or tissue according to the above embodiment (6), wherein the preservation solution is a vitrification solution containing 10 mass % or more of a cryoprotectant relative to the total mass of the preservation solution.

Advantageous Effects of Invention

The embodiment (1) provides a device for cryopreservation which enables easy recovery of a cell or tissue in thawing a frozen cell or tissue in the procedure of cryopreservation of the cell or tissue. The embodiments (2) to (4) provide a device for cryopreservation which enables particularly easy recovery of a cell or tissue in thawing a frozen cell or tissue. According to the embodiment (5), not only the above effects can be obtained, but also the preservation solution absorber absorbs an excess preservation solution surrounding a cell or tissue when the cell or tissue is deposited on the deposition part of the device for cryopreservation. Thus, the embodiment provides a device for cryopreservation of a cell or tissue which enables easy and simple cryopreservation of a cell or tissue without the need of additional procedures for removing the excess preservation solution (for example, downward suction removal through the preservation solution absorber or direct suction removal from the periphery of the cell or tissue using a micropipette). The embodiments (6) and (7) provide a cryopreservation method which enables easy release and recovery of a cell or tissue after cryopreservation.

DESCRIPTION OF EMBODIMENTS

Figure 1:
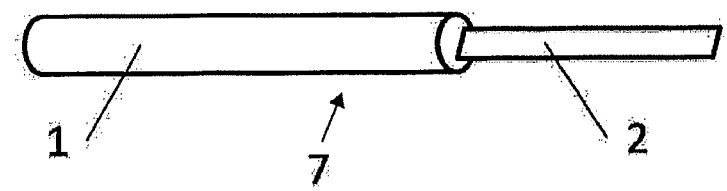
FIG. 1 is an overall view illustrating one example of the device for cryopreservation of a cell or tissue of the present invention.

The device for cryopreservation of the present invention is used for cryopreserving a cell or tissue. The "cell" herein encompasses not only a single cell but also a biological cell population composed of multiple cells. The cell population composed of multiple cells may be a cell population composed of a single kind of cells or may be a cell population composed of multiple kinds of cells. The tissue may be composed of a single kind of cells or may be composed of multiple kinds of cells, or may contain a non-cellular substance like an extracellular matrix in addition to cells.

The device for cryopreservation of the present invention is used for cryopreservation, preferably for vitrification cryopreservation. The device for cryopreservation of the present invention is thus suitably used as a device for vitrification cryopreservation of a cell or tissue. Specifically, the device for cryopreservation of the present invention is to be used in a process including immersing and freezing a device for cryopreservation holding a cell or tissue in a coolant such as liquid nitrogen. The cell or tissue deposited on the device for cryopreservation is thawed by taking out the cell or tissue from coolant together with the device for cryopreservation and immersing them into a thawing solution. In cryopreservation with the device for cryopreservation of the present invention, a cell or tissue is usually deposited together with a preservation solution on a layer containing a water-soluble polymeric compound of the deposition part. The device for cryopreservation of the present invention can reliably hold the deposited cell or tissue, and also allows easy recovery of the cell or tissue in thawing. The use of the device thus enables easy and reliable cryopreservation of a cell or tissue. The device for cryopreservation of the present invention can be said in different words, such as a tool for cryopreservation of a cell or tissue, a tool for preservation of a cell or tissue, an instrument for cryopreservation of a cell or tissue, and an instrument for preservation of a cell or tissue.

The device for cryopreservation of the present invention includes a deposition part on which a cell or tissue is to be deposited, the deposition part having a layer containing a water-soluble polymeric compound (hereinafter, also referred to as "surface layer according to the present invention" or simply as "surface layer") on an outermost surface of the deposition part. This surface layer is preferably soluble in a thawing solution. The "soluble" herein means that the surface layer has a solubility of 0.2 mass % or higher in a thawing solution at 25° C. As mentioned above, the device for cryopreservation of the present invention is to be used in the following manner. In the freezing procedure, a cell or tissue is deposited together with a preservation solution on the layer containing a water-soluble polymeric compound of the device for cryopreservation, and then immersed and frozen in a coolant (e.g., liquid nitrogen). In thawing, the frozen cell or tissue is taken out together with the device for cryopreservation and immersed and thawed in a thawing solution. During thawing of the cell or tissue, the layer containing a water-soluble polymeric compound is entirely or partly dissolved into the thawing solution, which enables easy release and recovery of the cell or tissue without it adhering to the deposition part of the device for cryopreservation.

In the present invention, the deposition part preferably has a preservation solution absorber and preferably has the layer containing a water-soluble polymeric compound (surface layer) on the preservation solution absorber.

When the deposition part of the device for cryopreservation of the present invention has a preservation solution absorber and has the surface layer according to the present invention on the outermost surface of the deposition part, not only the above effects can be obtained but also the preservation solution absorber absorbs an excess preservation solution, thus eliminating the need for additional procedures of removing the excess preservation solution. This significantly improves the working efficiency. The cell or tissue after such a procedure is covered with a very small amount of the preservation solution and thus can be quickly frozen in the freezing procedure. The vitrification cryopreservation, as mentioned above, has the disadvantage of chemical toxicity due to a large amount of cryoprotectant contained in the preservation solution. With the device for cryopreservation in which the deposition part has a preservation solution absorber, the amount of vitrification solution around the deposited cell or tissue is very small, so that an improved viability of the cell or tissue is expected. The deposition part having a preservation solution absorber preferably has no other layer between the preservation solution absorber and the surface layer.

In the following, the configuration of the device for cryopreservation of the present invention is described.

The device for cryopreservation of the present invention includes a deposition part on which a cell or tissue is to be deposited, the deposition part having a layer containing a water-soluble polymeric compound on an outermost surface of the deposition part. The outermost surface of the deposition part on which a cell or tissue is to be deposited herein corresponds to a surface portion on which a cell or tissue is deposited together with a preservation solution. In the present invention, the deposition part preferably has the surface layer according to the present invention on a non-absorbing support (e.g., various resin films, metal, glass, or rubber) or a preservation solution absorber, particularly preferably on a preservation solution absorber. Here, the surface layer according to the present invention does not have to form a uniform layer throughout the entire deposition part on which a cell or tissue is to be deposited. For example, the surface layer may be in an island-in-sea form or a stripe form. In other words, it is important that the surface layer according to the present invention is present on the outermost surface of the portion on which a cell or tissue is deposited together with a preservation solution, but the surface layer may or may not be present in the portion on which the cell or tissue is not deposited. The deposition part thus may have the surface layer on the entire outermost surface or on a part of the outermost surface.

In the present invention, examples of the water-soluble polymeric compound contained in the surface layer include cellulose derivatives such as hydroxyethylcellulose and carboxymethylcellulose, starch and derivatives thereof, gelatin, casein, alginic acid and salt thereof, polyvinyl alcohol, polyvinylpyrrolidone, styrene-maleic acid copolymer salts, and styrene-acrylic acid copolymer salts. Preferred among these are alginic acid and salts thereof and gelatin because they are soluble in the preservation solution and has an appropriate film formation effect. Particularly preferred is polyvinyl alcohol because it is a non-biological material and less toxic to a cell or tissue. These water-soluble polymeric compounds may be used alone or in combination of two or more thereof. The surface layer may contain a cross-linking agent in the range that does not reduce the solubility of the surface layer in the thawing solution to below 10 mass %. The "water soluble" in the water-soluble polymeric compound of the present invention means that the solubility in water at 25° C. is at least 0.5 mass %. The solubility in water at 25° C. of the water-soluble polymeric compound is more preferably 5 mass % or higher.

The solids content of the water-soluble polymeric compound contained in the surface layer is preferably 0.01 to 100 g/m$^2$, more preferably 0.1 to 10 g/m$^2$. The solids content of the water-soluble polymeric compound of more than 100 g/m$^2$ is undesirable because it results in an increased dissolution and mixing of the water-soluble polymeric compound into the thawing solution. The solids content of the water-soluble polymeric compound of less than 0.01 g/m$^2$ may prevent the easy release of a cell or tissue in thawing.

In the present invention, the surface layer preferably contains at least one selected from the group consisting of a polyvinyl alcohol having an ethanediol group and a polyvinyl alcohol having an ethylene oxide group, as the water-soluble polymeric compound. The polyvinyl alcohol having an ethanediol group and the polyvinyl alcohol having an ethylene oxide group form a film having an excellent hydrophilicity, an appropriate strength, and an appropriate solubility. These properties enable particularly easy release and recovery of a cell or tissue without it adhering to the deposition part in the thawing procedure. As the polyvinyl alcohol having an ethanediol group and the polyvinyl alcohol having an ethylene oxide group, those with various degrees of saponification can be used. Still, in order to obtain good releasability of a cell or tissue, these polyvinyl alcohols preferably have a degree of saponification of 94 mol % or less. These polyvinyl alcohols may be used alone or in combination of two or more thereof. The polyvinyl alcohol having an ethanediol group and the polyvinyl alcohol having an ethylene oxide group may be those commercially available from The Nippon Synthetic Chemical Industry Co., Ltd., for example.

When the surface layer contains at least one polyvinyl alcohol selected from the group consisting of a polyvinyl alcohol having an ethanediol group and a polyvinyl alcohol having an ethylene oxide group, the surface layer may contain other one or two or more water-soluble polymeric compounds. Examples of the water-soluble polymeric compounds include cellulose derivatives such as hydroxyethylcellulose and carboxymethylcellulose, starch and derivatives thereof, gelatin, casein, alginic acid and salt thereof, polyvinyl alcohol free from an ethanediol group and an ethylene oxide group, polyvinylpyrrolidone, styrene-maleic acid copolymer salts, and styrene-acrylic acid copolymer salts. The amount of such other water-soluble polymeric compound(s) is preferably 50 mass % or less relative to the solids content of the at least one polyvinyl alcohol selected from the group consisting of a polyvinyl alcohol having an ethanediol group and a polyvinyl alcohol having an ethylene oxide group.

In the present invention, the surface layer preferably contains a polyvinyl alcohol with a degree of saponification of 94 mol % or less as the water-soluble polymeric compound. The use of a film containing the polyvinyl alcohol with a degree of saponification of 94 mol % or less as the surface layer results in excellent releasability of a cell or tissue, which enables easy recovery of a cell or tissue without it adhering to the deposition part in the thawing procedure. Furthermore, choosing a polyvinyl alcohol with a degree of saponification of 81 mol % or less or choosing a polyvinyl alcohol with a degree of saponification of 94 mol % or less and a degree of polymerization of 400 or less results in a device for cryopreservation in which the releasability of a cell or tissue is particularly excellent. These polyvinyl alcohols may be used alone or in combination of two or more thereof.

When the surface layer contains a polyvinyl alcohol with a degree of saponification of 94 mol % or less, the surface layer may contain other one or two or more water-soluble polymeric compounds. Examples of the water-soluble polymeric compounds include cellulose derivatives such as hydroxyethylcellulose and carboxymethylcellulose, starch and derivatives thereof, gelatin, casein, alginic acid and salt thereof, polyvinyl alcohol with a degree of saponification of more than 94 mol %, polyvinylpyrrolidone, styrene-maleic acid copolymer salts, and styrene-acrylic acid copolymer salts. The amount of such other water-soluble polymeric compound(s) is preferably 50 mass % or less relative to the solids content of the polyvinyl alcohol with a degree of saponification of 94 mol % or less.

In the present invention, the surface layer preferably contains inorganic fine particles in addition to the above water-soluble polymeric compound. The inorganic fine particles do not reduce the hydrophilicity of the surface layer, and form fine irregularities on the surface layer that can reduce the contact area of the deposition part with a cell or tissue. As a result, the cell or tissue can be more easily released and recovered without it adhering to the deposition part of the device for cryopreservation.

Examples of the inorganic fine particles include precipitated calcium carbonate, heavy calcium carbonate, magnesium carbonate, kaolin, titanium dioxide, zinc oxide, zinc hydroxide, calcium silicate, magnesium silicate, noncrystalline synthetic silica, alumina, alumina hydrate, and magnesium hydroxide. The inorganic fine particles preferably have an average particle size (average secondary particle size in the case of inorganic fine particles in which primary particles are aggregated into secondary aggregates, average primary particle size in the case of inorganic fine particles not forming secondary particles) of 1 µm or smaller, more preferably 600 nm or smaller. The lower limit of the average particle size of the inorganic fine particles is not limited, but is preferably 6 nm or greater. In the case of the inorganic fine particles in which primary particles are aggregated into secondary aggregates, for example, the average particle size can be determined as the number median diameter with a laser-scattering particle size distribution analyzer (e.g., LA910, HORIBA, Ltd.). In the case of the inorganic fine particles not forming secondary particles, the average particle size can be determined using an electron micrograph of particles dispersed to such an extent that their primary particle size can be determined. Specifically, the average particle size can be determined as the average particle size of 100 particles present in a certain area in the micrograph. Particularly preferred are inorganic fine particles in which primary particles do not aggregate and thus not form secondary particles (hereinafter referred to as "inorganic fine particles dispersible in a single particle form") because with such inorganic fine particles the contact area of the deposition part with a cell or tissue is a relatively small. Colloidal silica is suitable from such a viewpoint. Examples of the colloidal silica include SNOWTEX (registered trademark) commercially available from Nissan Chemical Industries, Ltd. Also preferred is colloidal silica in which the particle surface is coated with polyvinylpyrrolidone, such as Percoll (trade name) available from GE Healthcare Japan.

In the present invention, when the deposition part has a preservation solution absorber (described later), the layer containing the water-soluble polymeric compound and inorganic fine particles is preferably formed on the outermost surface of the deposition part without blocking the pores in the preservation solution absorber with the inorganic fine particles. In order to achieve this, the particle size of the inorganic fine particles may be greater than the pore size of the preservation solution absorber, or the inorganic fine particles may be present inside the pores as long as the absorbency of the preservation solution absorber is not significantly reduced.

The solids content of the inorganic fine particles in the device for cryopreservation of the present invention is preferably 0.01 to 100 $g/m^2$, more preferably 0.1 to 10 $g/m^2$. The solids content of the inorganic fine particles of more than 100 $g/m^2$ is undesirable because it results in an increased dissolution and mixing of the inorganic fine particles into the thawing solution. The solids content of the inorganic fine particles of less than 0.01 $g/m^2$ may prevent the easy release of a cell or tissue in thawing.

In the present invention, when the surface layer further contains inorganic fine particles in addition to the water-soluble polymeric compound described above, the content ratio of the inorganic fine particles to the water-soluble polymeric compound (total mass of inorganic fine particles/total mass of water-soluble polymeric compounds) is preferably 1 to 100, more preferably 1.67 to 50. When the content ratio of the inorganic fine particles to the water-soluble polymeric compound is within this range, the surface (surface layer) of the deposition part can maintain appropriate irregularities, enabling easy recovery of a cell or tissue in the thawing procedure. In addition, such a content ratio prevents, for example, falling (powder falling) of the inorganic fine particles before use of the device for cryopreservation or accidental falling of the inorganic fine particles during dropwise deposition of a vitrification solution in the freezing procedure.

In the present invention, preferably, the deposition part has a support for supporting a cell or tissue when it is cryopreserved, and has the surface layer on the support. Examples of such a support (non-absorbing support) include various resin films, metal, glass, and rubber. The support may be made of one material or two or more materials. In particular, resin films are suitable from the viewpoint of the handling. Specific examples of the resin films include those made from polyester resin such as polyethylene terephthalate (PET) and polyethylene naphthalate (PEN), acrylic resin, epoxy resin, silicone resin, polycarbonate resin, diacetate resin, triacetate resin, polyacrylate resin, polyvinyl chloride resin, polysulfone resin, polyether sulfone resin, polyimide resin, polyamide resin, polyolefin resin, and cyclic polyolefin resin. The support preferably has a total light transmittance of 80% or higher in order to facilitate checking of the cell or tissue deposited on the deposition part under a transmission microscope. Metal supports, which have excellent thermal conductivity and enable quick freezing, can also be suitably used. Specific examples of metal supports include copper, copper alloy, aluminum, aluminum alloy, gold, gold alloy, silver, silver alloy, iron, and stainless steel. The support preferably has a thickness of 10 µm to 10 mm. The surface of the support may be subjected to easy adhesion treatment by an electric method such as corona discharge treatment or a chemical method, according to the purpose. The surface of the support may be roughened. One or more other layers may be provided between the support and the surface layer. Alternatively, the surface layer may be provided on the front side of the support and one or more other layers may be provided on the back side. The surface layer may be formed on each of the front and back of the support. The support may be a preservation solution absorber (described later).

The following will describe the case where the device for cryopreservation of the present invention has the layer containing the water-soluble polymeric compound on a preservation solution absorber.

As described above, when the deposition part for a cell or tissue in the present invention has a preservation solution absorber, the preservation solution absorber can remove the preservation solution even if a large amount of the preservation solution adheres to a cell or tissue. This eliminates the need for procedures of removing the preservation solution, thus significantly improving the working efficiency. The cell or tissue after such a procedure is covered with a very small amount of the preservation solution and thus can be quickly frozen in the freezing procedure. In the vitrification cryopreservation mentioned above, an aqueous solution containing a large amount of cryoprotectant such as glycerol, ethylene glycol, dimethyl sulfoxide (DMSO) is used as the preservation solution, and such a preservation solution is chemically toxic due to the large amount of cryoprotectant. With the device for cryopreservation in which the deposition part has the preservation solution absorber, the deposited cell or tissue is surrounded by a very small amount of the vitrification solution, so that an improved viability of the cell or tissue is expected. Accordingly, the device for cryopreservation in which the deposition part has the layer containing a water-soluble polymeric compound on the preservation solution absorber is suitable as a device for vitrification cryopreservation.

In the present invention, when the deposition part has the preservation solution absorber, preferably the surface layer is formed on the outermost surface of the deposition part without blocking the pores in the preservation solution absorber. The surface layer may be present inside the pores in the preservation solution absorber as long as the absorbency of the preservation solution absorber is not significantly reduced.

In the present invention, when the deposition part has the preservation solution absorber, a greater solids content of the surface layer leads to narrower pores in the preservation solution absorber, and thus tends to lead to a lower preservation solution absorbency. In contrast, a greater solids content of the surface layer leads to a greater releasability of a cell or tissue in the thawing procedure. The solids content of the surface layer when the deposition part has the preservation solution absorber can be appropriately adjusted in view of the balance of these properties, and is preferably 0.1 to 5 g/m$^2$, although it depends on the thickness, pore size, and porosity of the preservation solution absorber used.

Examples of the preservation solution absorber in the device for cryopreservation of the present invention include various sheets such as fibrous sheets, porous resin sheets, porous metal sheets, and porous metal oxide sheets. The term "porous" herein means that the sheet is a structure having pores (small cavities) on the surface thereof. The sheet is more preferably a structure having open pores on the surface of and inside the sheet. The preservation solution absorber (any of the above various sheets) preferably has a thickness of 10 μm to 5 mm, more preferably 20 μm to 2.5 mm. When the preservation solution absorber is a thin sheet, the above-mentioned non-absorbing support may be used as an enforcement member.

In the present invention, the fibrous sheet to be used as the preservation solution absorber may be paper or nonwoven fabric, for example. The paper preferably satisfies that the proportion of binding agent components such as a binder in the whole paper is 10 mass % or less, more preferably 5 mass % or less, still more preferably 3 mass % or less. This leads to excellent preservation solution absorbency. The proportion of papermaking chemicals contained in the paper in the entire paper is preferably 1 mass % or less. Chemicals such as fluorescent brighteners, dyes, and cationic sizing agents among papermaking chemicals usually contained in paper may disadvantageously affect cells.

When the fibrous sheet is paper, it preferably has a density of 0.1 to 0.6 g/cm$^3$ and a grammage of 10 to 130 g/m$^2$. The paper preferably has a density of 0.12 to 0.3 g/cm$^3$ and a grammage of 10 to 100 g/m$^2$ in order to provide a device for cryopreservation having excellent preservation solution absorbency as well as providing such an excellent visibility of a cell or tissue that the cell or tissue deposited on the deposition part can be observed under a transmission microscope.

If the fibrous sheet is nonwoven fabric, examples of the fiber contained in the nonwoven fabric include cellulose fiber, rayon fiber and cupro fiber which are regenerated fibers made from cellulose fiber, acetate fiber which is a semi-synthetic fiber made from cellulose fiber, polyester fiber, nylon fiber, acrylic fiber, polypropylene fiber, polyethylene fiber, polyvinyl chloride fiber, vinylidene fiber, polyurethane fiber, vinylon fiber, glass fiber, and silk fiber. Nonwoven fabric made by mixing fibers among these fibers may also be used. Preferred are cellulose fiber, rayon fiber and cupro fiber which are cellulose regenerated fibers derived from cellulose fiber, as well as acetate fiber which is a semi-synthetic fiber made from cellulose fiber.

When the fibrous sheet is nonwoven fabric, it preferably has a density of 0.1 to 0.4 g/cm$^3$ and a grammage of 10 to 130 g/m$^2$. In order to provide a device for cryopreservation having excellent preservation solution absorbency as well as providing excellent visibility of a cell or tissue, the nonwoven fabric preferably has a density of 0.12 to 0.3 g/cm$^3$ and a grammage of 10 to 100 g/m$^2$.

Similar to the case of paper as mentioned above, nonwoven fabric to be used as the preservation solution absorber also preferably satisfies that the proportion of binding agent components such as a binder in the whole nonwoven fabric is 10 mass % or less, more preferably 5 mass % or less, still more preferably 3 mass % or less. The nonwoven fabric is preferably free from a binding agent.

Unlike paper, nonwoven fabric may be produced by various methods. The nonwoven fabric with a reduced proportion of binding agent components is preferably produced by spun-bonding or melt-blowing, and preferably produced by aligning fibers by a wet process or a dry process, and then performing hydroentanglement or needle punching. As mentioned above, the fiber contained in the nonwoven fabric in the present invention is preferably cellulose fiber, rayon fiber or cupro fiber which is a cellulose regenerated fiber derived from cellulose fiber, or acetate fiber which is a semi-synthetic fiber made from cellulose fiber. If the nonwoven fabric is produced using such a fiber, the production method is preferably hydroentanglement or needle punching regardless of whether the fibers are aligned by a wet process or a dry process.

Examples of the porous resin sheet to be used as the preservation solution absorber in the present invention include resin sheets having a porous structure which is formed of a microfibrous structure prepared by at least uniaxially stretching a resin material and heating the resin material up to a temperature of not lower than the melting point of the resin to sinter the resin material, as disclosed in JP S42-13560 B and JP H08-283447 A; and a resin sheet having a porous structure which is formed by putting solid powder of thermoplastic resin prepared by, for example, emulsion polymerization or pulverization into a mold, heating and sintering the powdery particles to fuse the surfaces of the particles, and then cooling the particles, as disclosed in JP 2009-235417 A. Using a porous resin sheet as the preservation solution absorber is preferred because it enables production of a device for cryopreservation having excellent preservation solution absorbency as well as providing excellent visibility of a cell or tissue.

Examples of the resin constituting the porous resin sheet include polyethylene species such as low-density polyethylene, high-density polyethylene, and ultra high molecular weight polyethylene, polypropylene, polymethyl methacrylate, polystyrene, fluororesins such as polytetrafluoroethylene and polyvinylidene difluoride, ethylene-vinyl acetate copolymers, polyamide, styrene-acrylonitrile copolymers, styrene-butadiene-acrylonitrile terpolymers, polycarbonate, and polyvinyl chloride. In particular, fluororesins such as polytetrafluoroethylene and polyvinylidene difluoride advantageously allow the porous resin sheet to have a high transparency when a cell or tissue is deposited on the deposition part together with the preservation solution such as a vitrification solution. Such a high transparency significantly improves the visibility of the cell or tissue under a transmission microscope, makes it possible to provide a device for cryopreservation particularly excellent in the visibility of a cell or tissue. The porous resin sheet may be a membrane filter for filtering which is commercially available for the purposes of physical and chemical experiments and researches.

In the present invention, the porous metal sheet to be used as the preservation solution absorber may be a porous metal sheet made from a metal such as copper, copper alloy, aluminum, aluminum alloy, gold, gold alloy, silver, silver alloy, tin, zinc, lead, titanium, nickel, or stainless steel. The porous metal oxide sheet may be preferably a porous metal oxide sheet made from a metal oxide such as silica, alumina, zirconium, or quartz glass. The porous metal sheet and the porous metal oxide sheet each may be a porous sheet containing two or more of the metals or the metal oxides. The porous metal oxide sheet is preferred because it enables production of a device for cryopreservation providing excellent visibility of a cell or tissue.

In the present invention, each of the porous metal sheet and the porous metal oxide sheet to be used as the preservation solution absorber may be produced by a commonly known method. The porous metal sheet to be used as the vitrification solution absorber may be produced by powder metallurgy or the spacer method. Also, what is called the powder space holder method, which is a combination of resin injection molding and powder metallurgy, may preferably be used. For example, methods disclosed in WO 2006/041118 and JP 4578062 B may be used. Specifically, metal power and a resin serving as a spacer are mixed, and then the mixture is pressure-molded and fired in a high-temperature environment so that the metal powder is sintered and the resin serving as a spacer is evaporated. Thereby, a porous metal sheet is obtained. In the case of the powder space holder method, for example, a resin binder may also be mixed with the metal powder and the resin serving as a spacer. Alternatively, other methods of producing metal porous bodies, such as melt foaming and gas expansion, may be used in which metal powder is heated at high temperature and gas is injected to form voids. Methods of producing metal porous bodies using a foaming agent, such as slurry foaming, may also be used. The porous metal oxide sheet to be used as the preservation solution absorber may be produced by, for example, methods disclosed in JP 2009-29692 A and JP 2002-160930 A.

In order to improve its compatibility with the surface layer, the surface of the porous body selected from the above porous resin sheets, porous metal sheets, porous metal oxide sheets, and the like, may be hydrophilized. The hydrophilization may be achieved by, for example, graft modification, coating with a hydrophilic substance that does not dissolve out, or other common surface modification using any of various energies such as corona discharge, plasma treatment, and excimer laser.

If the preservation solution absorber in the present invention is a porous body selected from the above porous resin sheets, porous metal sheets, porous metal oxide sheets, and the like, the porous body preferably has a pore size of 0.02 to 130 µm, more preferably 0.05 to 60 µm. If the pore size is smaller than 0.02 µm, the performance of absorbing the preservation solution may be insufficient when the preservation solution is deposited dropwise. Further, the porous sheet may be difficult to produce. If the pore size is greater than 130 µm, the performance of absorbing the preservation solution may be insufficient. The pore size of the porous body, in the case of a porous resin sheet, corresponds to the diameter of the greatest pore measured by the bubble point test. In the case of a porous metal sheet or a porous metal oxide sheet, the pore size corresponds to the average pore diameter determined by image observation of the surface and cross section of the porous body.

The preservation solution absorber preferably has a porosity of 20 vol % or more, more preferably 30 vol % or more. When the preservation solution absorber is a porous body selected from the above porous resin sheets, porous metal sheets, porous metal oxide sheets, and the like, the pores inside the porous body preferably form a continuous structure not only in the thickness direction but also in the direction perpendicular to the thickness direction. Such a structure enables effective use of the pores inside the porous body, leading to good performance of absorbing the preservation solution. The thickness of the preservation solution absorber and the porosity of the porous body may be appropriately selected in accordance with factors such as the type of a cell or tissue used and the amount of the preservation solution deposited dropwise with the cell or tissue.

The porosity is defined by the following formula. The void volume V can be determined as the value per unit area ($m^2$) by multiplying the cumulative pore volume (mL/g) by the dry solids content ($g/m^2$) of the preservation solution absorber. The cumulative pore volume is the total volume of pores having a pore radius of 3 nm to 400 nm in the preservation solution absorber and is determined by measurement and data processing with a mercury porosimeter (name: Autopore II 9220, Micromeritics Instrument Corporation). The thickness T of the preservation solution absorber can be measured on a photograph of the cross section of the preservation solution absorber taken with an electron microscope.

$P=(V/T)\times 100(\%)$
P: porosity (%)
V: void volume ($mL/m^2$)
T: thickness (µm)

When the deposition part has the non-absorbing support as an enforcement member in addition to the preservation solution absorber, an adhesive layer may be formed between the preservation solution absorber and the non-absorbing support. The adhesive layer may contain an adhesive composition such as an instant adhesive composition typified by a moisture-curable adhesive substance, a hot-melt adhesive composition, or a photo-curable adhesive composition. Preferred examples thereof include compositions containing any of water-soluble polymeric compounds such as polyvinyl alcohol, hydroxycellulose, polyvinyl pyrrolidone, and starch paste; and water-insoluble resins such as vinyl acetate resin, acrylic resin, epoxy resin, urethane resin, elastomeric resin, cyanoacrylate resin, fluorine resin, silicone resin, nitrocellulose resin, nitrile rubber resin, styrene-butadiene resin, urea resin, styrene resin, phenolic resin, polyimide resin, polyamide resin, polyester resin, bismaleimide resin, olefinic resin, and EVA resin. The adhesive layer may contain one resin or may contain multiple resins. The adhesive layer preferably has a solids content of 0.01 to 100 g/m$^2$, more preferably 0.1 to 50 g/m$^2$.

The area of the deposition part of the device for cryopreservation of the present invention may be appropriately determined in accordance with factors such as the amount of the preservation solution deposited dropwise with the cell or tissue, and may be any value. For example, the area thereof is preferably 1 mm$^2$ or larger, more preferably 2 to 400 mm$^2$ per microliter of the preservation solution deposited dropwise. If the deposition part in one device for cryopreservation has multiple preservation solution absorbers on the non-absorbing support, one continuous preservation solution absorber portion preferably has the above area.

The deposition part in the present invention may be produced by any method. For example, a deposition part having a surface layer on a support or a preservation solution absorber can be produced by forming a surface layer on a support or a preservation solution absorber. The surface layer according to the present invention may be produced by any method. For example, a coating liquid containing a water-soluble polymer is applied to a support or a preservation solution absorber and dried to form a surface layer on the support or the preservation solution absorber. When the surface layer contains inorganic fine particles, the surface layer can be formed with a coating liquid containing a water-soluble polymer and inorganic fine particles. The coating liquid may contain a solvent such as water or an organic solvent. The coating liquid may be applied by any appropriately selected method.

The deposition part of the device for cryopreservation of the present invention has been described above. The device for cryopreservation of the present invention may include a handle together with the deposition part. The presence of the handle advantageously leads to good working efficiency in the cryopreservation and thawing procedures.

FIG. 1 is an overall view illustrating one example of the device for cryopreservation of a cell or tissue of the present invention. In FIG. 1, a device for cryopreservation 7 includes a handle 1 and a deposition part 2.

The handle is preferably made from a liquid nitrogen-resistant material. Preferred examples of such a material include various metals such as aluminum, iron, copper, and stainless steel alloy, ABS resin, polypropylene resin, polyethylene resin, fluorine resin, various engineering plastics, and glass. In FIG. 1, the handle 1 has a cylindrical shape. Still, the handle may have any shape. As will be mentioned later, in some cases, a cap may be placed on the deposition part 2 holding a cell or tissue before freezing so as to avoid direct contact between the cell or tissue and liquid nitrogen. In this case, the handle 1 may be tapered such that the diameter of the cylinder continually decreases from the side with no deposition part 2 to the side with the deposition part 2, thereby improving the working efficiency when placing a cap. The deposition part 2 is preferably in the form of a strip or sheet for easy handling.

The following describes a method for connecting the handle 1 and the deposition part 2 as illustrated in FIG. 1. If the handle 1 is made from resin, the deposition part 2 may be connected to the handle 1 by insert molding in the course of molding processing, for example. Alternatively, the deposition part 2 may be connected to the handle 1 using an adhesive by forming a structure-inserting part (not illustrated) in the handle 1. Various adhesives may be used, and preferred are silicone or fluorine adhesives which are resistant to low temperatures.

Figure 2:
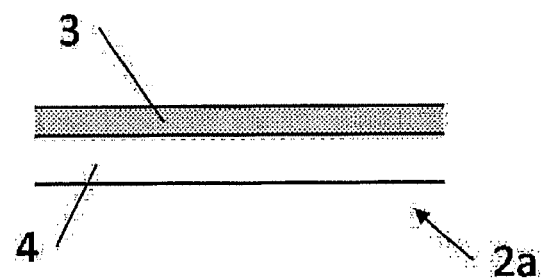
FIG. 2 is a schematic cross-sectional view illustrating one example of a deposition part in FIG. 1.

FIG. 2 is a schematic cross-sectional view illustrating one example of a deposition part in FIG. 1. In FIG. 2, a deposition part 2a has a surface layer 3 on a support 4. The deposition part 2a with such a structure can be obtained by, for example, applying a coating liquid containing a water-soluble polymeric compound on the support by a slide hopper method or dip coating.

Figure 3:
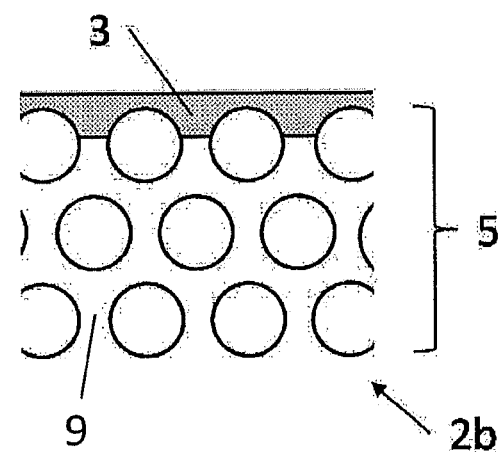
FIG. 3 is a schematic cross-sectional view illustrating one example where the deposition part illustrated in FIG. 1 has a preservation solution absorber.
Figure 4:
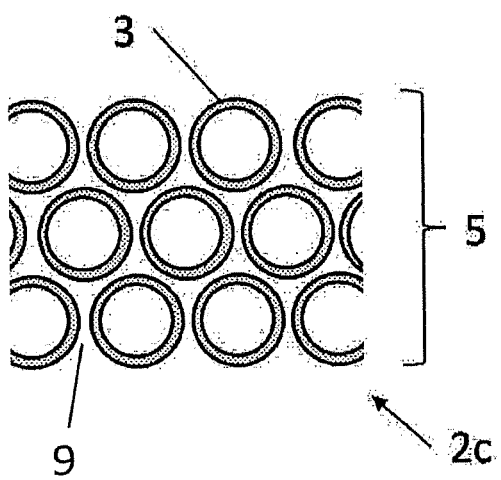
FIG. 4 is a schematic cross-sectional view showing another example where the deposition part illustrated in FIG. 1 has a preservation solution absorber.
Figure 5:
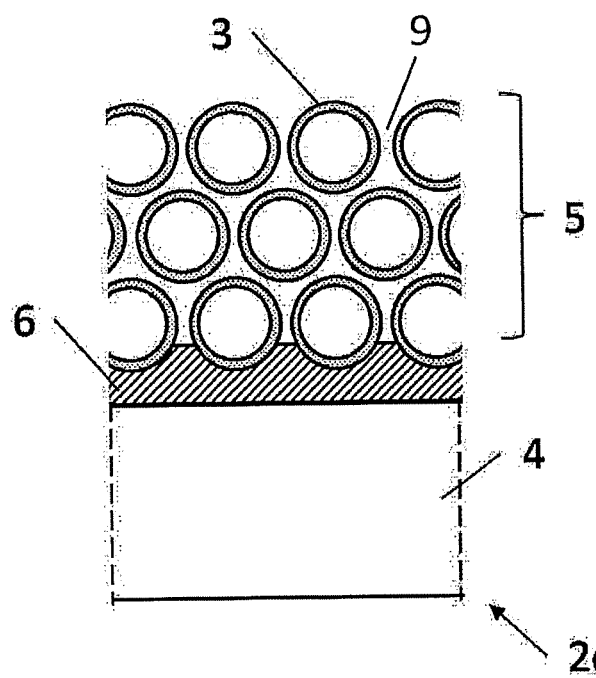
FIG. 5 is a schematic cross-sectional view illustrating still another example where the deposition part illustrated in FIG. 1 has a preservation solution absorber.

FIGS. 3 to 5 are schematic cross-sectional views each illustrating one example of a device for cryopreservation in which the deposition part has a preservation solution absorber and has a layer containing a water-soluble polymeric compound on the preservation solution absorber. A preservation solution absorber 5 in FIGS. 3 to 5 is a structure having pores (small cavities) 9. The cross-sections of the preservation solution absorber 5 in FIGS. 3 to 5 are merely for illustration and not limitation.

FIG. 3 is a schematic cross-sectional view illustrating one example where the deposition part illustrated in FIG. 1 has a preservation solution absorber. In FIG. 3, a deposition part 2b has the preservation solution absorber 5 and the surface layer 3 on the preservation solution absorber 5. The deposition part 2b with such a structure can be obtained by, for example, applying the above coating liquid to the preservation solution absorber by a slide hopper method.

FIG. 4 is a schematic cross-sectional view showing another example where the deposition part illustrated in FIG. 1 has a preservation solution absorber. In FIG. 4, a deposition part 2c has the surface layer 3 in the entire porous body as the preservation solution absorber 5. As illustrated in the figure, when the surface layer is present on the preservation solution absorber, the surface layer does not have to form a continuous layer on the surface of the preservation solution absorber, and may be present on the pore surface in the preservation solution absorber. This structure is preferred because the pores in the porous body are not blocked and thus both the vitrification solution absorbency in the freezing procedure and the releasability of a cell or tissue in the thawing procedure can be achieved. Also in this embodiment, microscopically the surface layer according to the present invention is present on the outermost surface of the deposition part. Thus, FIG. 4 illustrates one example of the present invention. The deposition part 2c with such a structure can be obtained by, for example, applying the above coating liquid by dip coating.

FIG. 5 is a schematic cross-sectional view illustrating still another example where the deposition part illustrated in FIG. 1 has a preservation solution absorber. In FIG. 5, a deposition part 2d has the surface layer 3 in the entire porous body as the preservation solution absorber 5 as illustrated in FIG. 4, and further has a support 4 and an adhesive layer 6. This structure enables more reliable freezing and thawing procedures even if, for example, the porous body used as the preservation solution absorber 5 has poor self-supportability.

Figure 6:
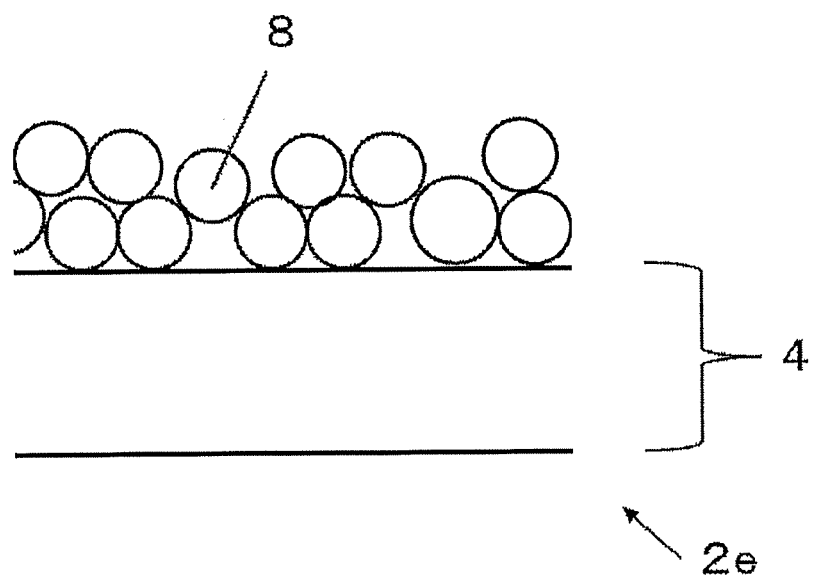
FIG. 6 is one example of a schematic cross-sectional view illustrating a deposition part with a surface layer containing inorganic fine particles.

FIG. 6 is one example of a schematic cross-sectional view illustrating a deposition part with a surface layer containing inorganic fine particles. In FIG. 6, a deposition part 2e has inorganic fine particles 8 arranged in the form of a layer on the support 4. The deposition part 2e with such a structure can be obtained by, for example, applying a coating liquid containing a water-soluble polymeric compound and inorganic fine particles on the support by a slide hopper method or a dip coating method.

Figure 7:
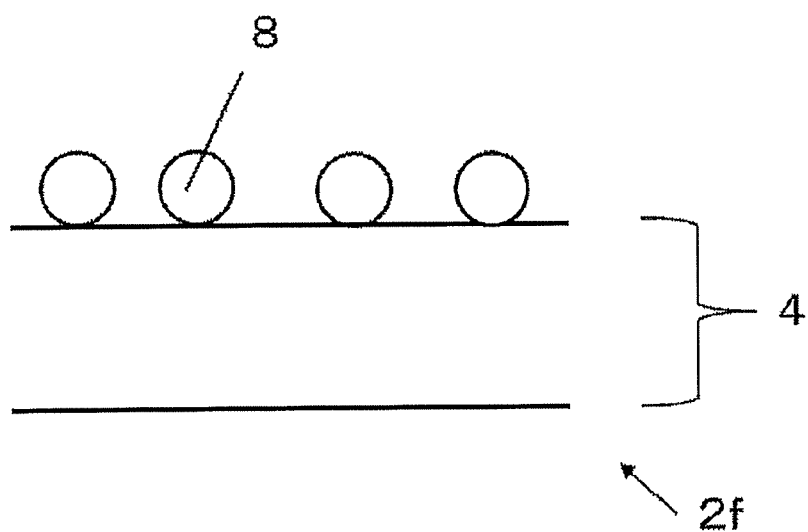
FIG. 7 is another example of a schematic cross-sectional view illustrating a deposition part with a surface layer containing inorganic fine particles.

FIG. 7 is another example of a schematic cross-sectional view illustrating a deposition part with a surface layer containing inorganic fine particles. In FIG. 7, a deposition part 2*f* has inorganic fine particles 8 interspersed on the support 4.

Figure 8:
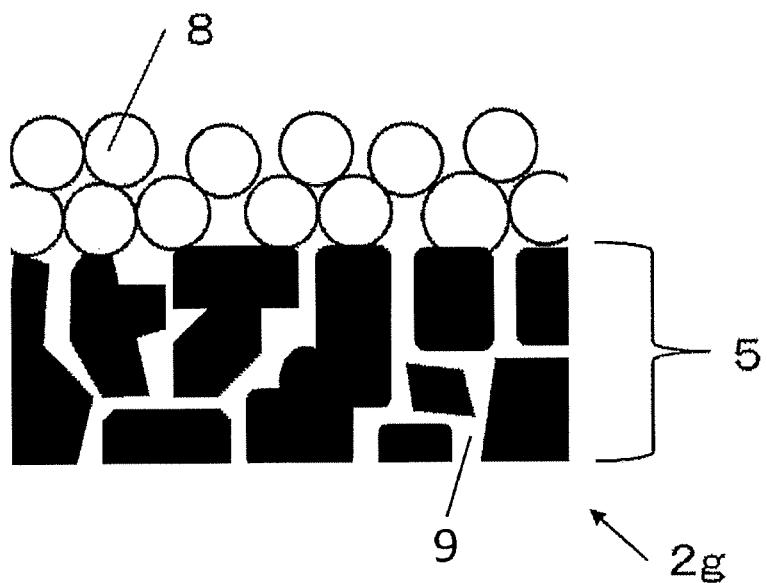
FIG. 8 is a schematic cross-sectional view illustrating one example where a deposition part has a preservation solution absorber, and a surface layer contains inorganic fine particles.

FIG. 8 is a schematic cross-sectional view illustrating one example where a deposition part has a preservation solution absorber, and a surface layer contains inorganic fine particles. In FIG. 8, a deposition part 2*g* has the inorganic fine particles 8 on the surface of the preservation solution absorber 5. The deposition part 2*g* with such a structure can be obtained using inorganic particles 8 having a particle size greater than pore size of the preservation solution absorber 5. Specifically, the deposition part 2*g* can be obtained by applying a coating liquid containing the inorganic fine particles 8 and a water-soluble polymeric compound by such an application method as the slide hopper method or the dip coating method mentioned above.

Figure 9:
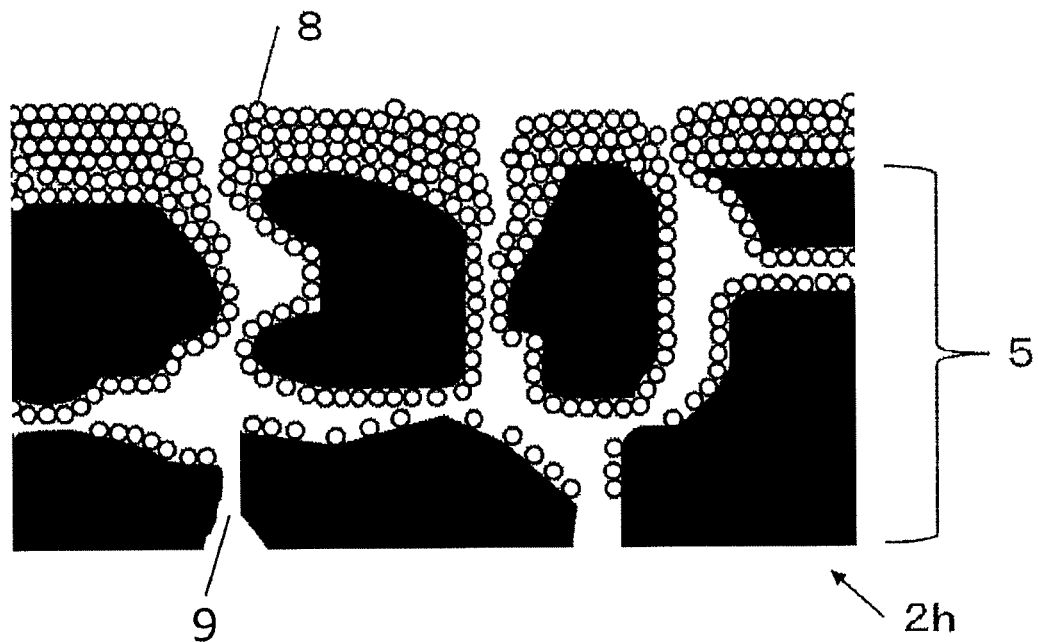
FIG. 9 is a schematic cross-sectional view illustrating another example where a deposition part has a preservation solution absorber, and a surface layer contains inorganic fine particles.

FIG. 9 is a schematic cross-sectional view illustrating another example where a deposition part has a preservation solution absorber, and a surface layer contains inorganic fine particles. In FIG. 9, a deposition part 2*h* has the inorganic fine particles 8 both on the outermost surface of the preservation solution absorber 5 and inside pores in the preservation solution absorber 5. The deposition part 2*h* with such a structure can be obtained using inorganic particles 8 having a particle size smaller than the pore size of the preservation solution absorber 5. Specifically, the deposition part 2*h* can be obtained by applying a coating liquid containing the inorganic fine particles 8 and a water-soluble polymeric compound by such an application method as the slide hopper method or the dip coating method mentioned above. Even when the inorganic fine particles 8 have a particle size smaller than pore size of the preservation solution absorber 5, the pore size is reduced because of the inorganic fine particles 8 entering the pores. Thus, as illustrated in FIG. 9, the inorganic fine particles may be arranged in the form of a layer on the surface of the preservation solution absorber 5. The schematic cross-sectional views of FIGS. 6 to 9 each illustrate one example of a deposition part having a layer containing a water-soluble polymeric compound and inorganic fine particles on the outermost surface. In FIGS. 6 to 9, the surface layer 3 (water-soluble polymeric compound) is omitted, and only inorganic fine particles 8 are shown.

In long-term cryopreservation of a cell or tissue using the device for cryopreservation of a cell or tissue of the present invention, as mentioned above, the cell or tissue may be covered with a cap or the device for cryopreservation may be sealed in a container in any form to be isolated from the outside environment. A cell or tissue frozen by direct contact with non-sterile liquid nitrogen is not always guaranteed to be in a sterilized condition even if the device for cryopreservation is sterilized. Thus, the deposition part holding a cell or tissue is occasionally covered with a cap or the device for cryopreservation is sealed in a container before the freezing procedure so as not to cause direct contact of a cell or tissue with liquid nitrogen. Such a freezing method without direct contact with liquid nitrogen is the mainstream in developed countries such as European countries. For this reason, the cap and the container are preferably made from any of liquid nitrogen-resistant material such as various metals, various resins, glass, and ceramics. They may have any shape as long as they are not brought into contact with the deposition part and can shield a cell or tissue from the outside environment. The cap may have any shape, such as a half-spindle-shaped or dome-shaped cap like a cap for pencils, or a cylindrical straw cap. The container may be any one capable of including or storing the device for cryopreservation to seal it without contact with the cell or tissue deposited and may have any shape.

In the present invention, the device for cryopreservation may be used in combination with such a cap or container capable of shielding a cell or tissue on the deposition part from the outside environment as long as the effects of the present invention are not impaired. The device for cryopreservation used in combination with such a cap or container is also included in the present invention.

The device for cryopreservation of the present invention may be preferably used in the Cryotop method, for example. The conventional Cryotop method is usually used for storage of a single cell or a small number of cells (e.g., less than 10 cells). In contrast, the device for cryopreservation of the present invention can also be suitably used for storage of a larger number of cells (e.g., storage of 10 to 1000000 cells). It can also be suitably used for storage of sheet-like cells (what is called cell sheets) formed from multiple cells. The use of device for cryopreservation of the present invention enables easy recovery of a cell or tissue in thawing a frozen cell or tissue in the cryopreservation procedure. Additionally, since the deposition part has the preservation solution absorber, not only the above effect can be achieved, but also an excess vitrification solution surrounding the cell or tissue is absorbed in freezing the cell or tissue. Thus, the cell or tissue in thawing or freezing is less susceptible to damage due to the vitrification solution outside the cell, and can be cryopreserved with excellent viability.

Any method may be used for cryopreserving a cell or tissue using the device for cryopreservation of the present invention. For example, first, a cell or tissue immersed in a preservation solution is deposited dropwise onto the deposition part together with the preservation solution. An excess preservation solution surrounding the cell or tissue is preferably removed with a pipette or the like as much as possible. When the deposition part of the device for cryopreservation has a preservation solution absorber, this procedure is unnecessary as the excess preservation solution is automatically removed. Next, the device for cryopreservation with the cell or tissue held on the deposition part is immersed in liquid nitrogen or the like to freeze the cell or tissue. The cap described above capable of shielding the cell or tissue on the deposition part from the outside environment may be attached to the deposition part, or the device for cryopreservation may be sealed into the container described above before the device is immersed in liquid nitrogen or the like.

The present invention also includes such a method of cryopreservation of a cell or tissue including: depositing a cell or tissue immersed in a preservation solution on the deposition part of the device for cryopreservation of a cell or tissue together with the preservation solution; and immersing the device for cryopreservation with the cell or tissue held on the deposition part into liquid nitrogen to freeze the cell or tissue.

The preservation solution may be one usually used for freezing cells, such as eggs and embryos. For example, the preservation solution may be the aforementioned preservation solution prepared by adding a cryoprotectant (e.g., glycerol or ethylene glycol) to a physiological solution such as a phosphate buffered saline, or a vitrification solution containing a large amount (at least 10 mass % or more, more preferably 20 mass % or more relative to the total mass of the preservation solution) of a cryoprotectant such as glycerol, ethylene glycol, or dimethyl sulfoxide (DMSO). In particular, the preservation solution is preferably a vitrification solution containing 10 mass % or more of a cryoprotectant relative to the total mass of the preservation solution. In the thawing procedure, the device for cryopreservation is taken out from the coolant such as liquid nitrogen and the deposition part holding the frozen cell or tissue is immersed in a thawing solution. The cell or tissue is then recovered.

Examples of the cell that can be cryopreserved using the device for cryopreservation of the present invention include reproductive cells such as eggs, embryos, and sperms from mammals (for example, human, bovine, swine, equine, leporine, rat, and mouse); and pluripotent stem cells such as induced pluripotent stem cells (iPS cells) and embryonic stem cells (ES cells). Also included are culture cells such as primary culture cells, subculture cells, and cell lines. In one or more embodiments, examples of the cell include adhesive cells such as fibroblasts, cancer-derived cells (e.g., pancreatic cancer cells and hepatoma cells), epithelial cells, vascular endothelial cells, lymphatic endothelial cells, neuronal cells, chondrocytes, tissue stem cells, and immune cells. Examples of the tissue that can be cryopreserved include tissues formed of homologous cells and tissues formed of heterologous cells, such as tissues of ovary, skin, corneal epithelium, periodontal ligament, and myocardium. The present invention is particularly suitable for cryopreservation of tissues having a sheet-like structure (e.g., cell sheets and skin tissues). The device for cryopreservation of the present invention can be suitably used for cryopreservation of not only native tissues harvested from living bodies but also artificial tissues, such as cultured skins obtained by in vitro growth of cells, what is called cell sheets formed in vitro, and a three-dimensional tissue model described in JP 2012-205516 A. The device for cryopreservation of the present invention is suitably used as a device for cryopreservation of the aforementioned cells or tissues.

EXAMPLES

The present invention is specifically described in more detail below with reference to examples. The present invention, however, should not be limited to the examples below.

Example 1

A transparent PET film (total light transmittance 91%, haze 5.5%) which had been subjected to easy adhesion treatment was provided as a support. Onto the support was applied a 5 mass % aqueous solution of high purity polyvinyl alcohol EG-05P (The Nippon Synthetic Chemical Industry Co., Ltd., degree of saponification 86.5 to 89 mol %) by a slide hopper method to achieve a dry solids content of 5 g/m$^2$. The workpiece was dried at room temperature to produce a deposition part as illustrated in FIG. 2. This deposition part was cut into a size of 2 mm×20 mm (40 mm$^2$) and connected to an ABS resin-made handle, thus producing a device for cryopreservation of Example 1 as illustrated in FIG. 1.

Comparative Example 1

A device for cryopreservation of Comparative Example 1 was produced in the same manner as in the production of the device for cryopreservation in Example 1 except that the transparent PET film was used as is as the deposition part.
<Mouse Egg Freezing Procedure>

An egg harvested from a mouse was immersed in a modified phosphate buffer (137 mM NaCl, 2.7 mM KCl, 0.9 mM CaCl$_2$.2H$_2$O, 0.5 mM MgCl$_2$.6H$_2$O, 1.5 mM KH$_2$PO$_4$, 8 mM Na$_2$HPO$_4$. 5.6 mM glucose, 0.3 mM sodium pyruvate, 65 µg/mL dibekacin sulfate, 1 mg/mL polyvinylpyrrolidone, 14.8 mM L-proline, 200 mM trehalose) at 15° C. for 10 minutes. The modified buffer contained phenol red at a very low concentration as a pH indicator. Thereafter, the mouse egg was taken out and then immersed in a 15° C. equilibration solution (7 vol % ethylene glycol, 0.5 vol % glycerol, 92.5 vol % the modified phosphate buffer) for 5 minutes. Subsequently, the mouse egg was taken out from the equilibration solution and immersed in a 4° C. vitrification solution (30 vol % ethylene glycol, 0.5 vol % glycerol, 69.5% the modified phosphate buffer, 0.5 M sucrose). After the immersion into the vitrification solution for 30 seconds, the mouse egg was deposited on the deposition part of the device for cryopreservation of Example 1 or Comparative Example 1. An excess vitrification solution around the mouse egg was removed as much as possible with a pipette while observing under a transmission microscope. The device was then immersed in liquid nitrogen and vitrified. The frozen device for cryopreservation was stored in a liquid nitrogen storage container until thawing.
<Mouse Egg Thawing Procedure and Releasability Evaluation>

The device for cryopreservation holding the mouse egg of Example 1 or Comparative Example 1 was taken out from liquid nitrogen and immersed in a 37° C. thawing solution (a solution prepared by adding 1 M sucrose to the modified phosphate buffer). The mouse egg thus immersed was observed under a transmission light microscope, and the releasability of the mouse egg in thawing was evaluated according to the following criteria. The results are shown in the section of "Releasability in thawing" in Table 1.

The releasability in thawing was evaluated according to the following criteria.

Very good: When the device for cryopreservation was immersed in the thawing solution, the mouse egg was released by slightly shaking the handle (the mouse egg was released within one minute).

Good: When the device for cryopreservation was immersed in the thawing solution, the mouse egg was released by shaking the handle side to side or up and down (the mouse egg was released within one minute).

Poor: The mouse egg was not released within one minute by shaking the handle side to side or up and down.

TABLE 1

|  | Releasability in thawing |
| --- | --- |
| Example 1 | Very good |
| Comparative Example 1 | Poor |

The results in Table 1 indicate that excellent releasability in thawing was obtained in the device for cryopreservation of the present invention.

Example 2

A transparent PET film (total light transmittance 91%, haze 5.5%) which had been subjected to easy adhesion treatment was provided as a support. Onto the support was applied hot melt urethane resin Purmelt QR 170-7141P (Henkel Japan Ltd.) as an adhesive layer to achieve a dry solids content of 30 g/m$^2$. Before the adhesive layer was completely solidified, hydrophilized porous polytetrafluoroethylene (Advantec Toyo Kaisha, Ltd., pore size 0.2 μm, porosity 71%, thickness 35 μm) as a preservation solution absorber was bonded thereto. The stack thus obtained was immersed in a 2 mass % aqueous solution of high purity polyvinyl alcohol EG-05P (The Nippon Synthetic Chemical Industry Co., Ltd., degree of saponification 86.5 to 89 mol %) for dip coating. The workpiece was dried at room temperature to produce a deposition part having a layer containing a water-soluble polymeric compound as illustrated in FIG. 5. The dry solids content of the applied layer containing a water-soluble polymeric compound was 1.6 g/m². The deposition part was cut into a size of 2 mm×20 mm and then connected to an ABS resin-made handle in the same manner as in Example 1, whereby producing a device for cryopreservation of Example 2 as illustrated in FIG. 1.

Example 3

A device for cryopreservation of Example 3 was produced in the same manner as in Example 2 except that the concentration of the aqueous solution of polyvinyl alcohol EG-05P was 1 mass %. The dry solids content of the applied layer containing a water-soluble polymeric compound in the device for cryopreservation of Example 3 was 0.5 g/m².

Example 4

A device for cryopreservation of Example 4 was produced in the same manner as in Example 2 except that the concentration of the aqueous solution of polyvinyl alcohol EG-059 was 0.2 mass %. The dry solids content of the applied layer containing a water-soluble polymeric compound in the device for cryopreservation of Example 4 was 0.1 g/m².

Example 5

A device for cryopreservation of Example 5 was produced in the same manner as in Example 2 except that the stack was immersed in a 1 mass % aqueous solution of PVA103 (Kuraray Co., Ltd., degree of saponification 98 to 99 mol %), which is another polyvinyl alcohol, to form a layer containing a water-soluble polymeric compound. The dry solids content of the applied layer containing a water-soluble polymeric compound in the device for cryopreservation of Example 5 was 0.5 g/m².

Example 6

A device for cryopreservation of Example 6 was produced in the same manner as in Example 2 except that the stack was immersed not in the aqueous solution of polyvinyl alcohol but in a 1 mass % aqueous solution of PN505 (Jellice), which is gelatin, to form a layer containing a water-soluble polymeric compound. The dry solids content of the applied layer containing a water-soluble polymeric compound in the device for cryopreservation of Example 6 was 0.5 g/m².

Example 7

Hydrophilized porous stainless steel (Taisei Kogyo Co., Ltd., pore size 1.5 μm, porosity 65%, thickness 1 mm) was used as a preservation solution absorber. It was immersed in a 1 mass % aqueous solution of polyvinyl alcohol EG-05P for dip coating. The workpiece was dried at room temperature to produce a deposition part having a layer containing a water-soluble polymeric compound as illustrated in FIG. 4. The dry solids content of the applied layer containing a water-soluble polymeric compound in Example 7 was 0.4 g/m². The deposition part was connected to an ABS resin-made handle in the same manner as in Example 1, whereby producing a device for cryopreservation of Example 7 as illustrated in FIG. 1.

Comparative Example 2

A device for cryopreservation of Comparative Example 2 without a layer containing a water-soluble polymeric compound was produced in the same manner as in the production of the device for cryopreservation of Example 2 except that the stack was not immersed in the aqueous solution. Specifically, the device for cryopreservation was produced by bonding hydrophilized porous polytetrafluoroethylene (pore size 0.2 μm, porosity 71%, thickness 35 μm) onto a transparent PET film (total light transmittance 91%, haze 5.5%) which had been subjected to easy adhesion treatment, via an adhesive layer (Henkel Japan Ltd., hot melt urethane resin Purmelt QR 170-7141P).

Comparative Example 3

A device for cryopreservation of Comparative Example 3 without a layer containing a water-soluble polymeric compound was produced in the same manner as in the production of the device for cryopreservation of Example 7 except that the stack was not immersed in the aqueous solution.

<Evaluation of Vitrification Solution Absorbency>

In the same manner as in the freezing procedure in Example 1 and Comparative Example 1, mouse eggs were immersed in a modified phosphate buffer, an equilibration solution, and a vitrification solution in sequence. The eggs were then deposited dropwise on the deposition parts of the devices for cryopreservation of Examples 2 to 7, Comparative Examples 2 and 3 together with 0.4 μL of the vitrification solution using STRIPPER pipette (ORIGIO). The state of the absorption of the vitrification solution after the dropwise deposition was observed under a microscope and evaluated according to the criteria below. For Examples 2 to 6 and Comparative Example 2, a transmission light microscope was used, and for Example 7 and Comparative Example 3, a reflection light microscope was used. The results are shown in the section of "Vitrification solution absorbency" in Table 2.

The vitrification solution absorbency was evaluated according to the following criteria.

Very good: The time from the dropwise deposition of the vitrification solution until an excess vitrification solution around the mouse egg was absorbed and no longer visible was less than 6 seconds.

Good: The time from the dropwise deposition of the vitrification solution until an excess vitrification solution around the mouse egg was absorbed and no longer visible was 6 to 30 seconds.

Poor: An excess vitrification solution around the mouse egg still remained at the time of 30 seconds after the dropwise deposition of the vitrification solution.

<Mouse Egg Thawing Procedure and Releasability Evaluation>

The thawing procedure and the releasability evaluation using the devices for cryopreservation of Examples 2 to 7 and Comparative Examples 2 and 3 were performed in the same manner as those using the devices for cryopreservation of Example 1 and Comparative Example 1 described earlier.

In the evaluation of Example 7 and Comparative Example 3, a reflection light microscope was used instead of a transmission light microscope. The results are shown in the section of "Releasability in thawing" in Table 2.

TABLE 2

|  | Vitrification solution absorbency | Releasability in thawing |
| --- | --- | --- |
| Example 2 | Good | Very good |
| Example 3 | Good | Good |
| Example 4 | Very good | Good |
| Example 5 | Good | Good |
| Example 6 | Good | Good |
| Example 7 | Good | Good |
| Comparative Example 2 | Very good | Poor |
| Comparative Example 3 | Very good | Poor |

The results in Table 2 indicate that excellent releasability in thawing as well as excellent vitrification solution absorbency was obtained in the device for cryopreservation of the present invention.

Example 8

A transparent PET film (total light transmittance 91%, haze 5.5%) which had been subjected to easy adhesion treatment was provided as a support. Onto the support was applied a 5 mass % aqueous solution of GOHSENX WO-320R (The Nippon Synthetic Chemical Industry Co., Ltd., degree of saponification 88.3 mol %), which is a polyvinyl alcohol having an ethylene oxide group, by a slide hopper method to achieve a dry solids content of 5 g/m². The workpiece was dried at room temperature and then heated at 120° C. for 40 hours to produce a deposition part having a surface layer on the support as illustrated in FIG. 2. The deposition part was cut into a size of 2 mm×20 mm (40 mm²) and connected to an ABS resin-made handle, whereby producing a device for cryopreservation of Example 8 as illustrated in FIG. 1.

Separately, a device for cryopreservation was produced in the same manner as in the production of the device for cryopreservation of Example 8 except that the transparent PET film was used as is as the deposition part. This device for cryopreservation is the same as that of Comparative Example 1, and thus referred to as "Comparative Example 1" in Table 3 below.

<Mouse Embryo Freezing Procedure>

A blastocyst stage embryo harvested from a mouse was immersed in a modified phosphate buffer (137 mM NaCl, 2.7 mM KCl, 0.9 mM $CaCl_2.2H_2O$, 0.5 mM $MgCl_2.6H_2O$, 1.5 mM $KH_2PO_4$, 8 mM $Na_2HPO_4$, 5.6 mM glucose, 0.3 mM sodium pyruvate, 65 μg/mL dibekacin sulfate, 1 mg/mL polyvinylpyrrolidone, 14.8 mM L-proline, 200 mM trehalose) at 15° C. for 10 minutes. The modified buffer contained phenol red at a very low concentration as a pH indicator. Thereafter, the mouse embryo was taken out and then immersed in a 15° C. equilibration solution (7.5 vol % dimethyl sulfoxide (DMSO), 7.5 vol % ethylene glycol, 17 vol % fetal bovine serum, 68 vol % the modified phosphate buffer) for 5 minutes. The mouse embryo was then taken out from the equilibration solution and immersed in a 4° C. vitrification solution (15 vol % dimethyl sulfoxide (DMSO), 15 vol % ethylene glycol, 14 vol % fetal bovine serum, 56 vol % the modified phosphate buffer, 0.5 M sucrose). After the immersion in the vitrification solution for 30 seconds, the mouse embryo was deposited on the deposition part of the device for cryopreservation of Example 8 or Comparative Example 1. An excess vitrification solution around the mouse embryo was removed as much as possible with a pipette while observing under a transmission microscope. The device was then immersed in liquid nitrogen and vitrified. The frozen device for cryopreservation was stored in a liquid nitrogen storage container until thawing.

<Mouse Embryo Thawing Procedure and Releasability Evaluation>

The device for cryopreservation of Example 8 or Comparative Example 1 holding the mouse embryo was taken out from liquid nitrogen and immersed in a 37° C. thawing solution (a solution prepared by adding 1 M sucrose to the modified phosphate buffer). The mouse embryo thus immersed was observed under a transmission light microscope, and the releasability of the mouse embryo in thawing was evaluated according to the following criteria. The results are shown in the section of "Releasability in thawing" in Table 3. Comparative Example 1 in Table 3, as mentioned above, is the device for cryopreservation in which the transparent PET film which had been subjected to easy adhesion treatment was used as is as the deposition part.

The releasability of a cell or tissue was evaluated according to the following criteria.

Very good: When the device for cryopreservation was immersed in the thawing solution, the mouse embryo was released by shaking the handle (the time required for the release was less than 20 seconds).

Good: When the device for cryopreservation was immersed in the thawing solution, the mouse embryo was released by shaking the handle (the time required for the release was 20 seconds or longer but less than 40 seconds).

Acceptable: When the device for cryopreservation was immersed in the thawing solution, it took 40 to 60 seconds to release the mouse embryo by shaking the handle.

Poor: The mouse embryo was not released within 60 seconds by shaking the handle.

TABLE 3

|  | Releasability of cell or tissue |
| --- | --- |
| Example 8 | Very good |
| Comparative Example 1 | Poor |

The results in Table 3 indicate that excellent releasability in thawing was obtained in the device for cryopreservation of the present invention.

Example 9

A transparent PET film (total light transmittance 91%, haze 5.5%) which had been subjected to easy adhesion treatment was provided as a support. Onto the support was applied hot melt urethane resin Purmelt QR 170-7141P (Henkel Japan Ltd.) as an adhesive layer to achieve a dry solids content of 30 g/m². Before the adhesive layer was completely solidified, hydrophilized porous polytetrafluoroethylene (Advantec Toyo Kaisha, Ltd., pore size 0.2 μm, porosity 71%, thickness 35 μm) as a preservation solution absorber was bonded thereto. The stack thus obtained was immersed in a 2 mass % aqueous solution of Nichigo-G polymer AZF8035W (The Nippon Synthetic Chemical Industry Co., Ltd., degree of saponification 98.4 mol %), which is a polyvinyl alcohol having an ethanediol group, for dip coating. The workpiece was dried at room temperature and then heated at 120° C. for 40 hours to produce a deposition part having a surface layer as illustrated in FIG. 5. The solids content of the surface layer was 1.6 g/m². The deposition part was cut into a size of 2 mm×20 mm and then connected to an ABS resin-made handle in the same manner as in Example 8, whereby producing a device for cryopreservation of Example 9 as illustrated in FIG. 1.

Example 10

A device for cryopreservation of Example 10 was produced in the same manner as in Example 9 except that a 2 mass % aqueous solution of Nichigo-G polymer OKS-8041 (The Nippon Synthetic Chemical Industry Co., Ltd., degree of saponification 88.9 mol %), which is a polyvinyl alcohol having an ethanediol group, was used for dip coating. The solids content of the surface layer of the device for cryopreservation of Example 10 was 1.6 g/m².

Example 11

A device for cryopreservation of Example 11 was produced in the same manner as in Example 9 except that a 2 mass % aqueous solution of GOHSENX WO-320R (degree of saponification 88.3 mol %), which is a polyvinyl alcohol having an ethylene oxide group, was used for dip coating. The solids content of the surface layer of the device for cryopreservation of Example 11 was 1.6 g/m².

Example 12

A device for cryopreservation of Example 12 was produced in the same manner as in Example 11 except that the concentration of the aqueous solution of GOHSENX WO-320R was 0.5 mass %. The solids content of the surface layer of the device for cryopreservation of Example 12 was 0.5 g/m².

Example 13

A device for cryopreservation of Example 13 was produced in the same manner as in Example 9 except that a 2 mass % aqueous solution of GOHSENX WO-320N (The Nippon Synthetic Chemical Industry Co., Ltd., degree of saponification 99 mol %), which is a polyvinyl alcohol having an ethylene oxide group, was used for dip coating. The solids content of the surface layer of the device for cryopreservation of Example 13 was 1.6 g/m².

Example 14

A device for cryopreservation of Example 14 was produced in the same manner as in Example 9 except that a 2 mass % aqueous solution of PVA103 (Kuraray Co., Ltd., degree of saponification 98.5 mol %), which is a polyvinyl alcohol, was used for dip coating. The solids content of the surface layer of the device for cryopreservation of Example 14 was 1.6 g/m².

Separately, a device for cryopreservation with no surface layer was produced as a comparative example in the same manner as in the production of the device for cryopreservation of Example 9 except that the stack was not immersed in the aqueous solution. This device for cryopreservation was produced by bonding hydrophilized porous polytetrafluoroethylene (pore size 0.2 µm, porosity 71%, thickness 35 µm) onto a transparent PET film (total light transmittance 91%, haze 5.5%) which had been subjected to easy adhesion treatment, via an adhesive layer (Henkel Japan Ltd., hot melt urethane resin Purmelt QR 170-7141P). The device for cryopreservation is the same as that of Comparative Example 2 above, and thus referred to as Comparative Example 2 in Table 4 below.

<Evaluation of Preservation Solution Absorbency>

In the same manner as in the freezing procedure in Example 8 and Comparative Example 1, mouse embryos were immersed in a modified phosphate buffer, an equilibration solution, and a vitrification solution in sequence. The mouse embryos were deposited dropwise on the deposition parts of the devices for cryopreservation of Examples 9 to 14 and Comparative Example 2 together with 0.3 µL of the vitrification solution using The STRIPPER pipette (ORIGIO). The state of the absorption of the vitrification solution after the dropwise deposition was observed under a reflection light microscope and evaluated according to the following criteria. The results are shown in the section of "Preservation solution absorbency" in Table 4 below.

The preservation solution absorbency was evaluated according to the following criteria.

Very good: The time from the dropwise deposition of the vitrification solution until an excess vitrification solution around the mouse egg was absorbed and no longer visible was less than 6 seconds.

Good: The time from the dropwise deposition of the vitrification solution until an excess vitrification solution around the mouse egg was absorbed and no longer visible was 6 to 30 seconds.

Poor: An excess vitrification solution around the mouse embryo still remained at the time of 30 seconds after the dropwise deposition of the vitrification solution.

<Mouse Embryo Thawing Procedure and Releasability Evaluation>

The thawing procedure and the releasability evaluation using the devices for cryopreservation of Examples 9 to 14 and Comparative Example 2 were performed in the same manner as those using the devices for cryopreservation of Example 8 and Comparative Example 1. The results are shown in the section of "Releasability of cell or tissue" in Table 4 below.

TABLE 4

|  | Preservation solution absorbency | Releasability of cell or tissue |
| --- | --- | --- |
| Example 9 | Good | Good |
| Example 10 | Good | Very good |
| Example 11 | Good | Very good |
| Example 12 | Very good | Good |
| Example 13 | Good | Good |
| Example 14 | Good | Acceptable |
| Comparative Example 2 | Very good | Poor |

The results in Table 4 indicate that excellent releasability in thawing as well as excellent vitrification solution absorbency was obtained in the device for cryopreservation of the present invention.

Example 15

A transparent PET film (total light transmittance 91%, haze 5.5%) which had been subjected to easy adhesion treatment was provided as a support. Onto the support was applied a 5 mass % aqueous solution of PVA505 (Kuraray Co., Ltd., degree of saponification 73.5 mol %, degree of polymerization 500), which is polyvinyl alcohol with a degree of saponification of 94 mol % or less, by a slide hopper method to achieve a dry solids content of 5 g/m². The workpiece was dried at room temperature and then heated at 120° C. for 40 hours to produce a deposition part having a surface layer on the support as illustrated in FIG. 2. The deposition part was cut into a size of 2 mm×20 mm (40 mm²) and connected to an ABS resin-made handle, whereby producing a device for cryopreservation of Example 15 as illustrated in FIG. 1.

Separately, a device for cryopreservation was produced in the same manner as in the production of the device for cryopreservation of Example 15 except that the transparent PET film was used as is as the deposition part. This device for cryopreservation is the same as that of Comparative Example 1 above, and thus is referred to as "Comparative Example 1" in Table 5 below.

<Mouse Embryo Freezing Procedure>

Mouse embryos were vitrified in the same manner as in the freezing procedure using the device for cryopreservation of Example 8 except that the devices for cryopreservation of Example 15 and Comparative Example 1 were used. The frozen devices for cryopreservation were stored in a liquid nitrogen storage container until thawing.

<Mouse Embryo Thawing Procedure and Releasability Evaluation>

The device for cryopreservation of Example 15 or Comparative Example 1 holding the mouse embryo was taken out from liquid nitrogen and immersed in a 37° C. thawing solution (a solution prepared by adding 1 M sucrose to the modified phosphate buffer). The mouse embryo thus immersed was thawed while observing under a transmission light microscope. In the thawing procedure, for 30 seconds immediately after immersing the mouse embryo on the device for cryopreservation in the thawing solution, the procedure of recovering the mouse embryo from the device for cryopreservation was not started and the mouse embryo on the device for cryopreservation was allowed to stand in the thawing solution. After 30 seconds, the recovery procedure was performed by shaking the handle of the device for cryopreservation to vibrate the deposition part or applying a suction pressure using a pipette. The procedure was continued until 60 seconds passed from the immersion of the mouse embryo in the thawing solution. The releasability of the mouse embryo in the thawing procedure was evaluated according to the following criteria. The results are shown in the section of "Releasability of cell or tissue" in Table 5.

The releasability of a cell or tissue was evaluated according to the following criteria.

Very good: The mouse embryo on the deposition part was easily released in the thawing procedure (the embryo was relatively smoothly released by simply shaking the handle side to side or up and down).

Good: The mouse embryo on the deposition part was released in the thawing procedure (the embryo was released by simply shaking the handle side to side or up and down).

Acceptable: The mouse embryo on the deposition part was released with some difficulty in the thawing procedure.

Poor: The mouse embryo was not released within 60 seconds.

TABLE 5

|  | Releasability of cell or tissue |
|---|---|
| Example 15 | Very good |
| Comparative Example 1 | Poor |

The results in Table 5 indicate that excellent releasability in the thawing procedure was obtained in the device for cryopreservation of the present invention.

Example 16

A transparent PET film (total light transmittance 91%, haze 5.5%) which had been subjected to easy adhesion treatment was provided as a support. Onto the support was applied hot melt urethane resin Purmelt QR 170-7141P (Henkel Japan Ltd.) as an adhesive layer to achieve a dry solids content of 30 g/m². Before the adhesive layer was completely solidified, hydrophilized porous polytetrafluoroethylene (Advantec Toyo Kaisha, Ltd., pore size 0.2 μm, porosity 71%, thickness 35 μm) as a preservation solution absorber was bonded thereto. The obtained stack was immersed in a 2 mass % aqueous solution of PVA505 (degree of saponification 73.5 mol %, degree of polymerization 500), which is polyvinyl alcohol with a degree of saponification of 94 mol % or less, for dip coating. The workpiece was dried at room temperature and then heated at 120° C. for 40 hours to produce a deposition part having a surface layer as illustrated in FIG. 5. The solids content of the surface layer was 1.6 g/m². The deposition part was cut into a size of 2 mm×20 mm and connected to an ABS resin-made handle in the same manner as in Example 15, whereby producing a device for cryopreservation of Example 16 as illustrated in FIG. 1.

Example 17

A device for cryopreservation of Example 17 was produced in the same manner as in Example 16 except that a 2 mass % aqueous solution of PVA217 (Kuraray Co., Ltd., degree of saponification 88 mol %, degree of polymerization 1700), which is a polyvinyl alcohol with a degree of saponification of 94 mol % or less, was used for dip coating. The solids content of the surface layer of the device for cryopreservation of Example 17 was 1.6 g/m².

Example 18

A device for cryopreservation of Example 18 was produced in the same manner as in Example 16 except that a 2 mass % aqueous solution of PVA205 (Kuraray Co., Ltd., degree of saponification 88 mol %, degree of polymerization 500), which is a polyvinyl alcohol with a degree of saponification of 94 mol % or less, was used for dip coating. The solids content of the surface layer of the device for cryopreservation of Example 18 was 1.6 g/m².

Example 19

A device for cryopreservation of Example 19 was produced in the same manner as in Example 16 except that a 2 mass % aqueous solution of GOSENOL EG03P (The Nippon Synthetic Chemical Industry Co., Ltd., degree of saponification 88 mol %, degree of polymerization 300), which is a polyvinyl alcohol with a degree of saponification of 94 mol % or less, was used for dip coating. The solids content of the surface layer of the device for cryopreservation of Example 19 was 1.6 g/m².

Example 20

A device for cryopreservation of Example 20 was produced in the same manner as in Example 16 except that a 2 mass % aqueous solution of PVA105 (Kuraray Co., Ltd., degree of saponification 98.5 mol %, degree of polymerization 500), which is a polyvinyl alcohol, was used for dip coating. The solids content of the surface layer of the device for cryopreservation of Example 20 was 1.6 g/m².

Separately, a device for cryopreservation with no surface layer was produced as a comparative example in the same manner as in the production of the device for cryopreservation of Example 16 except that the stack was not immersed in the aqueous solution. This device for cryopreservation was produced by bonding hydrophilized porous polytetrafluoroethylene (pore size 0.2 µm, porosity 71%, thickness 35 µm) onto a transparent PET film (total light transmittance 91%, haze 5.5%) which had been subjected to easy adhesion treatment, via an adhesive layer (Henkel Japan Ltd., hot melt urethane resin Purmelt QR 170-7141P). The device for cryopreservation is the same as that of Comparative Example 2 above, and thus referred to as Comparative Example 2 in Table 6 below.

<Evaluation of Preservation Solution Absorbency>

In the same manner as in the freezing procedure in Example 15 and Comparative Example 1, mouse embryos were immersed in a modified phosphate buffer, an equilibration solution, and a vitrification solution in sequence. The mouse embryos were deposited dropwise on the deposition parts of the devices for cryopreservation of Examples 16 to 20 and Comparative Example 2 together with 0.4 µL of the vitrification solution using The STRIPPER pipette (ORIGIO). The state of the absorption of the vitrification solution after the dropwise deposition was observed under a reflection light microscope and evaluated according to the following criteria. The results are shown in the section of "Preservation solution absorbency" in Table 6 below.

The preservation solution absorbency was evaluated according to the following criteria.

Good: An excess vitrification solution around the mouse embryo was absorbed within 30 seconds from the dropwise deposition of the vitrification solution.

Poor: An excess vitrification solution around the mouse embryo remained at the time of 30 seconds from the dropwise deposition of the vitrification solution.

<Mouse Embryo Thawing Procedure and Releasability Evaluation>

The thawing procedure and the releasability evaluation using the devices for cryopreservation of Examples 16 to 20 and Comparative Example 2 were performed in the same manner as those using the devices for cryopreservation of Example 15 and Comparative Example 1. The results are shown in the section of "Releasability of cell or tissue" in Table 6 below.

TABLE 6

| | Preservation solution absorbency | Releasability of cell or tissue |
|---|---|---|
| Example 16 | Good | Very good |
| Example 17 | Good | Good |
| Example 18 | Good | Good |

TABLE 6-continued

| | Preservation solution absorbency | Releasability of cell or tissue |
|---|---|---|
| Example 19 | Good | Very good |
| Example 20 | Good | Acceptable |
| Comparative Example 2 | Good | Poor |

The results in Table 6 indicate that excellent releasability in thawing as well as excellent vitrification solution absorbency was obtained in the device for cryopreservation of the present invention.

Example 21

A transparent PET film (total light transmittance 91%, haze 5.5%) which had been subjected to easy adhesion treatment was provided as a support. Onto the support was applied hot melt urethane resin Purmelt QR 170-7141P (Henkel Japan Ltd.) as an adhesive layer to achieve a dry solids content of 30 g/m². Before the adhesive layer was completely solidified, a porous cellulose mixed ester (Advantec Toyo Kaisha, Ltd., pore size 0.2 µm, porosity 73%, thickness 133 µm) as a preservation solution absorber was bonded thereto. The obtained stack was immersed in an aqueous solution (coating liquid) containing ST-ZL (Nissan Chemical Industries, Ltd., average particle size 85 nm), which is colloidal silica, in an amount of 20 mass % (silica concentration) and high purity polyvinyl alcohol EG-05P (The Nippon Synthetic Chemical Industry Co., Ltd., degree of saponification 86.5 to 89 mol %) in an amount of 1 mass % (polyvinyl alcohol solids concentration) for dip coating. The workpiece was dried at room temperature and further heated at 120° C. for one day to produce a deposition part having a water-soluble polymeric compound and inorganic fine particles on the surface. The coated amount of the inorganic fine particles in solids content was 3 g/m². The deposition part was cut into a size of 2 mm×20 mm (40 mm²) and connected to an ABS resin-made handle to produce a device for cryopreservation of Example 21 as illustrated in FIG. 1.

Example 22

<Preparation of Gas-Phase Silica Dispersion>
Water 430 parts
Modified ethanol 22 parts
Cationic polymer 3 parts
(dimethyldiallylammonium chloride homopolymer, Dai-ichi Kogyo Seiyaku Co., Ltd, SHALLOL DC902P, average molecular weight 9000)
Gas-phase silica 100 parts
(average primary particle size 7 nm, specific surface area measured by the BET method 300 m²/g)

Dimethyldiallylammonium chloride homopolymer was added to water and modified ethanol as dispersion media. Subsequently gas-phase silica was added and predispersed to prepare a coarse dispersion. The coarse dispersion was then treated twice with a high-pressure homogenizer to prepare a dispersion of gas-phase silica with a silica concentration of 20 mass %. The gas-phase silica had an average particle size of 100 nm.

A device for cryopreservation of Example 22 was produced in the same manner as in the production of the device for cryopreservation of Example 21 except that an aqueous solution containing the gas-phase silica dispersion in an amount of 10 mass % (silica concentration) and polyvinyl alcohol EG-05P in an amount of 1 mass % (polyvinyl alcohol solids concentration) was used. The coated amount of the inorganic fine particles in solids content was 3 g/m$^2$.

Example 23

A device for cryopreservation of Example 23 was produced in the same manner as in the production of the device for cryopreservation of Example 21 except that hydrophilized porous polytetrafluoroethylene (Advantec Toyo Kaisha, Ltd., pore size 0.2 μm, porosity 71%, thickness 35 μm), instead of the porous cellulose mixed ester, was bonded as the preservation solution absorber to the support via the adhesive layer. The coated amount of the inorganic fine particles in solids content was 3 g/m$^2$.

Example 24

A device for cryopreservation of Example 24 was produced in the same manner as in the production of the device for cryopreservation of Example 23 except that the coating liquid used for dip coating of the stack was an aqueous solution containing MP-4540 (Nissan Chemical Industries, Ltd., average particle size 450 nm), which is colloidal silica, in an amount of 5 mass % (silica concentration) and polyvinyl alcohol EG-05P in an amount of 2 mass % (polyvinyl alcohol solids concentration). The coated amount of the inorganic fine particles in solids content was 1 g/m$^2$.

Figure 10:
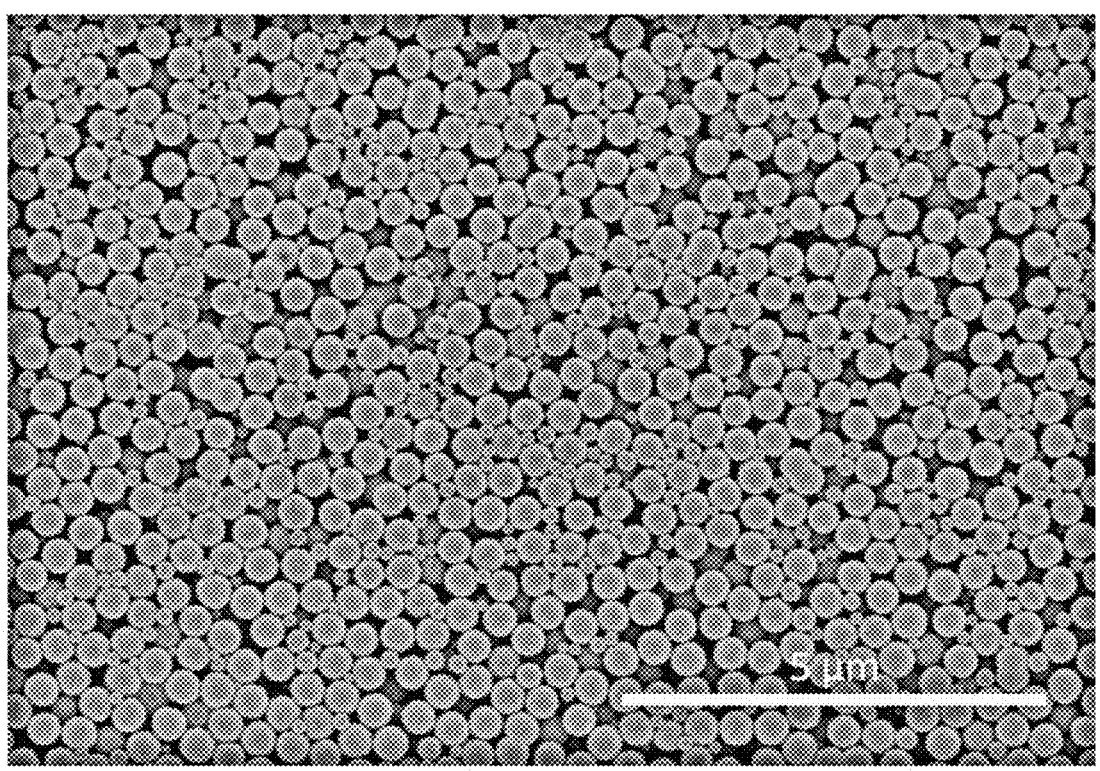
FIG. 10 is a scanning electron microscopic image of a surface of a deposition part of a device for cryopreservation of Example 24.

The surface of the device for cryopreservation of Example 24 was observed under a scanning electron microscope. The microscopic image as illustrated in FIG. 10 was obtained. In FIG. 10, the scale bar is 5 μm.

Example 25

A device for cryopreservation of Example 25 was produced in the same manner as in the production of the device for cryopreservation of Example 23 except that the coating liquid used for dip coating of the stack was an aqueous solution containing Percoll (GE Healthcare Japan, average particle size 30 nm), which is colloidal silica, in an amount of 20 mass % (silica concentration) and polyvinyl alcohol EG-05P in an amount of 1 mass % (polyvinyl alcohol solids concentration). The coated amount of the inorganic fine particles in solids content was 1 g/m$^2$.

Example 26

A device for cryopreservation of Example 26 was produced in the same manner as in the production of the device for cryopreservation Example 21 except that the transparent PET film (total light transmittance 91%, haze 5.5%) which had been subjected to easy adhesion treatment was used as the support, and that the support was dip-coated by immersion to a coating liquid similar to that in Example 21 and dried at room temperature. The solids content of the inorganic fine particles was 3 g/m$^2$.

Comparative Example 4

A device for cryopreservation of Comparative Example 4 was produced in the same manner as in the production of the device for cryopreservation of Example 21 except that the stack having a porous cellulose mixed ester as a preservation solution absorber was not dip-coated and used as is as the deposition part.

A device for cryopreservation was produced in the same manner as in the production of the device for cryopreservation of Example 21 except that the transparent PET film was used as is as the deposition part. This device for cryopreservation is the same as that of Comparative Example 1 above, and thus referred to as Comparative Example 1 in Table 7 below.

Separately, a device for cryopreservation was produced in the same manner as in the production of the device for cryopreservation of Example 23 except that the stack including the porous polytetrafluoroethylene was used as is as the deposition part without dip coating. This device for cryopreservation was produced by bonding hydrophilized porous polytetrafluoroethylene (pore size 0.2 μm, porosity 71%, thickness 35 μm) onto a transparent PET film (total light transmittance 91%, haze 5.5%) which had been subjected to easy adhesion treatment, via an adhesive layer (Henkel Japan Ltd., hot melt urethane resin Purmelt QR 170-7141P). The device for cryopreservation is the same as that of Comparative Example 2 above, and thus referred to as Comparative Example 2 in Table 7 below.

<Preparation of Human Hepatocyte Spheroid>

Human hepatocyte spheroids were prepared using PrimeSurface (registered trademark) 96 U plate (Sumitomo Bakelite Co., Ltd.). HepG2 cells were grown on Eagle's minimal essential medium (EMEM) supplemented with 10% of serum on a petri dish. The grown cells were released and recovered from the petri dish by trypsin treatment and seeded on the PrimeSurface 96 U plate at a cell concentration of 50 cells per well. After the cells were cultivated on the plate at 37° C. and 2% $CO_2$ for three days, formation of spheroids were confirmed. Spheroids having a nearly spherical shape and a diameter close to 100 μm were selected and used for the following evaluation.

<Spheroid Freezing Procedure>

For each of the devices for cryopreservation of Examples 21 to 26 and Comparative Examples 1, 2, and 4, one spheroid was immersed in a vitrification solution (30 vol % ethylene glycol, 0.5 vol % glycerol, 69.5% modified phosphate buffer (described below), 0.5 M sucrose) and deposited on the deposition part together with the vitrification solution. The freezing procedure in Examples 23 to 26 and Comparative Examples 1 and 2 was performed while observing the spheroid under a transmission microscope according to a conventional, common freezing procedure. The freezing procedure in Example 21, Example 22, and Comparative Example 4 was performed while observing the spheroid under a reflection microscope because of a low light transmittance of the deposition parts. As for the devices for cryopreservation having a preservation solution absorber, i.e., the devices for cryopreservation other than those of Example 26 and Comparative Example 1, it was confirmed under a transmission microscope or reflection microscope that the vitrification solution around the spheroid was sufficiently removed before the devices were immersed in liquid nitrogen for freezing. As for the devices for cryopreservation of Example 26 and Comparative Example 1, the vitrification solution around the spheroid was removed as much as possible with a pipette under a transmission microscope before the devices were immersed in liquid nitrogen for freezing.

<Thawing Procedure and Releasability Evaluation>

The devices for cryopreservation of Examples 21 to 26 and Comparative Examples 1, 2, and 4 holding the spheroid were taken out from liquid nitrogen and immersed in a 37° C. thawing solution (a solution prepared by adding 1 M sucrose to a modified phosphate buffer (137 mM NaCl, 2.7 mM KCl, 0.9 mM $CaCl_2.2H_2O$, 0.5 mM $MgCl_2.6H_2O$, 1.5 mM $KH_2PO_4$, 8 mM $Na_2HPO_4$, 5.6 mM glucose, 0.3 mM sodium pyruvate, 65 μg/mL dibekacin sulfate, 1 mg/mL polyvinylpyrrolidone, 14.8 mM L-proline, 200 mM trehalose)). While observing the state of the spheroid after immersion under a transmission light microscope or reflection microscope, the procedure for recovering the spheroid from the deposition part was performed with a pipette. The releasability of the spheroid in thawing was evaluated according to the following criteria. The results are shown in the section of "Releasability of cell or tissue" in Table 7.

Very good: When the device for cryopreservation was immersed in the thawing solution, the spheroid was released from the device within 30 seconds by shaking the handle side to side or up and down or pipetting.

Good: When the device for cryopreservation was immersed in the thawing solution, it took 30 seconds to 1 minute to release the spheroid from the device by shaking the handle side to side or up and down or pipetting.

Poor: The spheroid was not released within 1 minute.

TABLE 7

|  | Releasability of cell or tissue |
| --- | --- |
| Example 21 | Very good |
| Example 22 | Very good |
| Example 23 | Very good |
| Example 24 | Very good |
| Example 25 | Very good |
| Example 26 | Very good |
| Comparative Example 1 | Poor |
| Comparative Example 2 | Poor |
| Comparative Example 4 | Poor |

<Preservation Solution Absorbency>

One spheroid was immersed in a vitrification solution (30 vol % ethylene glycol, 0.5 vol % glycerol, 69.5% the above modified phosphate buffer, 0.5 M sucrose) and then deposited on the deposition part of the device for cryopreservation together with the vitrification solution. The preservation solution absorbency was evaluated upon the deposition. The devices for cryopreservation of Examples 21 to 25, which had a preservation solution absorber, had a good absorbency and needed no procedure for removing an excess vitrification solution using a pipette or the like. In particular Example 24 exhibited excellent absorbency; the excess vitrification solution was absorbed and removed within 10 seconds.

<Visibility of Cell or Tissue>

One spheroid was immersed in a vitrification solution (30 vol % ethylene glycol, 0.5 vol % glycerol, 69.5% the above modified phosphate buffer, 0.5 M sucrose) and then deposited on the deposition part of the device for cryopreservation together with the vitrification solution. At this time the spheroid was observed under a transmission microscope. The working efficiency during the observation was evaluated as the visibility of a cell or tissue. The devices for cryopreservation of Examples 23 to 26 allowed clearer observation of the deposited spheroid than the devices for cryopreservation of Examples 21 and 22.

INDUSTRIAL APPLICABILITY

The present invention can be applied to cryopreservation of cells or tissues such as cells or tissues for embryo transfer and artificial insemination of domestic animals (e.g., cattle) and other animals, and for human artificial insemination; iPS cells; ES cells; commonly used culture cells; cells or tissues harvested from living bodies for the purpose of examination or implantation; and cells or tissues cultured in vitro.

REFERENCE SIGNS LIST 1 handle
2, 2a to 2h deposition part
3 surface layer
4 support
5 preservation solution absorber
6 adhesive layer
7 device for cryopreservation
8 inorganic fine particles
9 pores (small cavities)

The invention claimed is:

1. A device for vitrification cryopreservation of a cell or tissue, comprising:
   a handle; and
   a deposition part on which a cell or tissue is to be deposited,
   wherein the handle is connected to the deposition part,
   wherein the deposition part comprises a preservation solution absorber and a layer containing a water-soluble polymeric compound on the preservation solution absorber,
   wherein the deposition part has no other layer between the preservation solution absorber and the layer containing a water-soluble polymeric compound,
   wherein the layer containing a water-soluble polymeric compound is on an outermost surface of the deposition part, and
   wherein the water-soluble polymeric compound is a polyvinyl alcohol with a degree of saponification of 94 mol % or less.

2. The device for vitrification cryopreservation of a cell or tissue according to claim 1,
   wherein the water-soluble polymeric compound is at least one selected from the group consisting of a polyvinyl alcohol having an ethanediol group and a polyvinyl alcohol having an ethylene oxide group.

3. The device for vitrification cryopreservation of a cell or issue according to claim 1,
   wherein the layer containing the water-soluble polymeric compound further contains inorganic fine particles.

4. The device for vitrification cryopreservation of a cell or issue according to claim 2, wherein the polyvinyl alcohol having an ethanediol group has the ethanediol group on a side chain and the polyvinyl alcohol having an ethylene oxide group has the ethylene oxide group on a side chain.

5. A method of cryopreservation of a cell or tissue, comprising: providing the device of claim 1, depositing a cell or tissue immersed in a preservation solution on the deposition part of the device for cryopreservation of the cell or tissue together with the preservation solution; and immersing the device with the cell or tissue held on the deposition part into liquid nitrogen to freeze the cell or tissue.

6. The method of cryopreservation of a cell or tissue according to claim 5,
   wherein the preservation solution is a vitrification solution containing 10 mass % or more of a cryoprotectant relative to the total mass of the preservation solution.

* * * * *